US011013783B2

(12) United States Patent
Langella et al.

(10) Patent No.: US 11,013,783 B2
(45) Date of Patent: May 25, 2021

(54) ANTI-INFLAMMATORY PEPTIDES AND METHODS FOR TREATING INFLAMMATORY DISEASES

(71) Applicant: INSTITUT NATIONAL DE LA RECHERCHE AGRONOMIQUE (INRA), Paris (FR)

(72) Inventors: Philippe Langella, Velizy-Villacoublay (FR); Benedicte Pigneur-Arnaud, Paris (FR); Jean-Marc Chatel, Meudon (FR); Elodie Quevrain, Le Perreux sur Marne (FR); Philippe Seksik, Paris (FR); Germain Trugnan, Montreuil (FR); Florian Chain, Versailles (FR); Luis G Bermudez-Humaran, Jouy en Josas (FR); Marie-Anne Maubert, Paris (FR); Christophe Michon, Livry-Gargan (FR); Harry Sokol, Paris (FR)

(73) Assignee: INSTITUT NATIONAL DE RECHERCHE POUR L'AGRICULTURE, L'ALIMENTATION ET L'ENVIRONNEMENT, Paris (FR)

( * ) Notice: Subject to any disclaimer, the term of this patent is extended or adjusted under 35 U.S.C. 154(b) by 223 days.

(21) Appl. No.: 15/802,910

(22) Filed: Nov. 3, 2017

(65) Prior Publication Data

US 2018/0085429 A1   Mar. 29, 2018

Related U.S. Application Data

(63) Continuation-in-part of application No. 14/655,439, which is a continuation of application No. PCT/EP2013/003917, filed on Dec. 26, 2013, now abandoned.

(30) Foreign Application Priority Data

Dec. 26, 2012   (EP) .................................... 12008611

(51) Int. Cl.
   *A61K 35/74*   (2015.01)
   *A61K 38/16*   (2006.01)
   *A61K 35/741*  (2015.01)

(52) U.S. Cl.
   CPC .......... *A61K 38/164* (2013.01); *A61K 35/741* (2013.01)

(58) Field of Classification Search
   None
   See application file for complete search history.

(56) References Cited

U.S. PATENT DOCUMENTS

| | | | |
|---|---|---|---|
| 4,861,719 A | 8/1989 | Miller | |
| 5,278,056 A | 1/1994 | Bank et al. | |
| 5,882,877 A | 3/1999 | Gregory et al. | |
| 6,013,516 A | 1/2000 | Verma et al. | |
| 6,127,175 A | 10/2000 | Vigne et al. | |
| 6,464,998 B1 | 10/2002 | Beuzard et al. | |

FOREIGN PATENT DOCUMENTS

| | | |
|---|---|---|
| WO | 9419478 | 9/1994 |
| WO | 9514785 | 6/1995 |
| WO | 9622378 | 7/1996 |

OTHER PUBLICATIONS

Keith et al., Nature Reviews, 2005, 4:1-8.
Goudy et al., International Reviews in Immunology, 2005, 24:307-326.
Factor, Molecular Therapy, 2003, 7:148-152.
Schneider et al., Annals of Allergy, Asthma & Immunology, 1998, 80: 263-268, Abstract.
Lewcowich et al., Eur. J. Immunol., 2002, 32: 3536-3545.
Hardy et al., Review, Science, 1998, 282: 1075-1079.
Atreya et al., J. Int. Med., 2008, 263: 591-596.
Sokol Harry et al.: "Faecalibacterium prausnitzii is an anti-inflammatory commensal bacterium identified by gut microbiota analysis of Crohn disease patients", Proceedings of the National Academy of Sciences, National Academy of Sciences, US, vol. 105, No. 43, Oct. 28, 2008 (Oct. 28, 2008), pp. 16731-16736, XP002579466, ISSN: 0027-8424, DOI: 10.1073/PNAS.0804812105 [retrieved on Oct. 20, 2008] the whole document.
Database Biosis [Online] Biosciences Information Service, Philadelphia, PA, US; May 2012 (May 2012), Rosique Rebeca Martin et al: "Protective and Curative Effect of Faecalibacterium prausnitzii in a Chronic DNBS-Induced Murine Colitis", XP002695881, Database accession No. PREV201200606260 abstract & Gastroenterology, vol. 142, No. 5, Suppl . 1, May 2012 (May 2012), p. 5392, Digestive Disease Week (DOW); San Diego, CA, USA; May 19-22, 2012 ISSN: 0016-5085 (print).
International Search Report, dated Apr. 7, 2014, from corresponding PCT application.
Communication regarding a Third-Party Submission issued in U.S. Appl. No. 16/072,319 dated Aug. 8, 2019.
Kechaou, N. et al., "Identification of One Novel Candidate Probiotic Lactobacillus plantarum Strain Active against Influenza Virus Infection in Mice by a Large-Scale Screening," Applied and Environmental Microbiology, Mar. 2013, vol. 79, No. 5, p. 1491-1499.

(Continued)

*Primary Examiner* — Ileana Popa
(74) *Attorney, Agent, or Firm* — Nixon & Vanderhye

(57) ABSTRACT

A method for preventing or treating an inflammatory disease, such as inflammatory bowel disease and Crohn disease, is presented. The method includes administering to a patient a polypeptide having the amino acid sequence of SEQ ID NO: 1, a conservative derivative or a fragment thereof, a nucleic acid sequence encoding said polypeptide, a vector comprising said nucleic acid sequence or a host cell that has been transfected, infected or transformed by said nucleic acid sequence and/or by said vector.

9 Claims, 7 Drawing Sheets

Specification includes a Sequence Listing.

(56) References Cited

OTHER PUBLICATIONS

Langella, "Commensal Bacteria and Recombinant Lactic Acid Bacteria as Novel Probiotics for Human Intestinal Health," pp. 1-61, Dec. 7, 2012, Vall d'Hebron Barcelona Hospital Institute of Research, slideshare.net, youtube.com, and web.archive.org.
Third-Party Submission filed in U.S. Appl. No. 16/072,319 dated Jul. 30, 2019.

```
M21/2      MMMPANFSAVSENEMTYVMGGS--------VADYLAPAMGAAQWQNFHKQLITIVGNKYVQGF
I-4873     MMMPANFSAVSENEMTYVMGGS--------IADYLAPAMGAAQWQNFHKQLVTIVGNKYVQGF
SL3-3      MMMPANFSAVSENEMTYVMGGS--------VADYLAPAMGAAQWQNFHKQLITIVGNKYVQGF
KLE1255    MMMPANFSAVAENEMTYVVGGS--------LVDVLAPAMITARMQNVSANVIKIVGNSFLAKY
CAG_821    MMMPANFSVVAENEMTYVVGGG-VIEAIGSVIAFIWTIANVKIENINLVTIIGNSYVSKL
CAG_822    MMMPANYSAIAENEMTYVVGGG-LLEAIGSVIAFVWGAANVKIFNTNLITIIGNSYVSKV
A2-165     MMMPANYSVIAENEMTYVNGGANFIDAIGAVTAPIWTLDNVKIFNTNIVILVGNTPLQST
L2-61      MMMPANFIAVN----SEVVYGGAELFTILASTTAPIWAANVKKFNTNLITLISNSFKKT
L2-62      MMMPANFSAVN---AEVVYG-----GAVADYLFSANTAESVKRFNSNIITLVGNSFISHL
           ******;:.:      * *       ;   ,..    , ) .  *(),::,*.)

M21/2      LDNTVGAMFSGTWTPGDGLIGFGSQFSTIWKKNYIENVIDESTGAQKFGYGALGVVNSIL
I-4873     LDNTVGAVFSGTWTPGVGLIGFGSQFSTIWKKNYIENVIDESTGAQKFGYGALGVVNSIL
SL3-3      LDNTVGAVFSGTWTPGDGLIGFGSQFSKIWKINYIDNVTGESTGAQKFGYGALGVVNSIL
KLE1255    INDVLAQLFDGNYVPGDVIGYSVKNLDKAYNKGYG--------IPGGNWGF-AVGALNAGM
CAG_821    VGATLGVMFGGNWGGDGPMSSFFGDNGSLSGIVKYG--------IAGSSKELNGFNKFM
CAG_822    LGATLGVMFSGAWGTKDDVAKAWGYDKDKKITIFGKNKALWNALDPNGDKEINGFNKFM
A2-165     INKIIGVLFSGNTTWKEVGNIGKNLFGIN--------------VKGNPIEKNNFGGYAM
L2-61      VSNTLGVMFGGMWGKDGDKIFGEEGSIRQNVFGLWM--------DGHTTRTDDMIFGNKVM
L2-62      LKAPLGIMFSGSWGSDGVTLFSDNG-----TFSGLYN--------VNRLPGGEAQTFGNKIM
                   .;, ;*.*                                           ;  ?

M21/2      NVAGNLAAIYNLGFGTAKNIVGEGVYKA--------------------
I-4873     NVAGNLAAIYNLGFGTAKNIVGEGVYKA--------------------
SL3-3      NVAGNLAAIYNLGFGTAKNIVGEGVYKA--------------------
KLE1255    QILGELSAIYTLGSSSIGLETKSSTLFTL-------------------
CAG_821    QVVGLGAAVYQLGTNKIKKTYWKVKTLGTTSKI---------------
CAG_822    QSIGALAAVYTLGTSTTKSNVAEGRYDVTSNGSF--------------
A2-165     KALSIRAAVYNLGVAPTKNTVKETEVKFTV------------------
L2-61      QVLGRAAVGYTLGTICAKVGFNDGVYGINGKL----------------
L2-62      TILGLASVVYTILGMKDAAVLTAKRVTNSNGQVWGDLPRNGGSGWVG
            *  ;, * **            .
```

Figure 3

SEQUENCE LISTING

```
<160> NUMBER OF SEQ ID NOS: 48

<210> SEQ ID NO 1
<211> LENGTH: 166
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (7)..(7)
<223> OTHER INFORMATION: X=F or Y
<220> FEATURE:
<221> NAME/KEY: MISC_FEATURE
<222> LOCATION: (8)..(8)
<223> OTHER INFORMATION: X= S or T
<220> FEATURE:
<221> NAME/KEY: MISC_FEATURE
<222> LOCATION: (9)..(9)
<223> OTHER INFORMATION: X= A or V
<220> FEATURE:
<221> NAME/KEY: MISC_FEATURE
<222> LOCATION: (10)..(10)
<223> OTHER INFORMATION: X= I or V
<220> FEATURE:
<221> NAME/KEY: MISC_FEATURE
<222> LOCATION: (11)..(11)
<223> OTHER INFORMATION: X= S, A or N
<220> FEATURE:
<221> NAME/KEY: MISC_FEATURE
<222> LOCATION: (12)..(12)
<223> OTHER INFORMATION: X= E or no amino acid
<220> FEATURE:
<221> NAME/KEY: MISC_FEATURE
<222> LOCATION: (13)..(13)
<223> OTHER INFORMATION: X= N or no amino acid
<220> FEATURE:
<221> NAME/KEY: MISC_FEATURE
<222> LOCATION: (14)..(14)
<223> OTHER INFORMATION: X= E or no amino acid
<220> FEATURE:
<221> NAME/KEY: MISC_FEATURE
<222> LOCATION: (15)..(15)
<223> OTHER INFORMATION: X= M, A or S
<220> FEATURE:
```

```
<221> NAME/KEY: MISC_FEATURE
<222> LOCATION: (16)..(16)
<223> OTHER INFORMATION: X= T or E
<220> FEATURE:
<221> NAME/KEY: MISC_FEATURE
<222> LOCATION: (17)..(17)
<223> OTHER INFORMATION: X= Y or V
<220> FEATURE:
<221> NAME/KEY: MISC_FEATURE
<222> LOCATION: (19)..(19)
<223> OTHER INFORMATION: X= M, V, N or Y
<220> FEATURE:
<221> NAME/KEY: MISC_FEATURE
<222> LOCATION: (21)..(21)
<223> OTHER INFORMATION: X= G or no amino acid
<220> FEATURE:
<221> NAME/KEY: MISC_FEATURE
<222> LOCATION: (22)..(22)
<223> OTHER INFORMATION: X= S, A, G or no amino acid
<220> FEATURE:
<221> NAME/KEY: MISC_FEATURE
<222> LOCATION: (23)..(23)
<223> OTHER INFORMATION: X= N, D or no amino acid
<220> FEATURE:
<221> NAME/KEY: MISC_FEATURE
<222> LOCATION: (24)..(24)
<223> OTHER INFORMATION: X= V, L, F or no amino acid
<220> FEATURE:
<221> NAME/KEY: MISC_FEATURE
<222> LOCATION: (25)..(25)
<223> OTHER INFORMATION: X= I, L, F or no amino acid
<220> FEATURE:
<221> NAME/KEY: MISC_FEATURE
<222> LOCATION: (26)..(26)
<223> OTHER INFORMATION: X= E, D, T, G or no amino acid
<220> FEATURE:
<221> NAME/KEY: MISC_FEATURE
<222> LOCATION: (27)..(27)
<223> OTHER INFORMATION: X= I, A or no amino acid
<220> FEATURE:
<221> NAME/KEY: MISC_FEATURE
<222> LOCATION: (28)..(28)
<223> OTHER INFORMATION: X= V, L or I
<220> FEATURE:
<221> NAME/KEY: MISC_FEATURE
<222> LOCATION: (29)..(29)
<223> OTHER INFORMATION: X= A, v or G
<220> FEATURE:
<221> NAME/KEY: MISC_FEATURE
<222> LOCATION: (30)..(30)
<223> OTHER INFORMATION: X=A, D or S
<220> FEATURE:
<221> NAME/KEY: MISC_FEATURE
<222> LOCATION: (31)..(31)
<223> OTHER INFORMATION: X= Y, V or T
<220> FEATURE:
<221> NAME/KEY: MISC_FEATURE
<222> LOCATION: (32)..(32)
<223> OTHER INFORMATION: X= L or T
<220> FEATURE:
<221> NAME/KEY: MISC_FEATURE
<222> LOCATION: (33)..(33)
<223> OTHER INFORMATION: X= A or P
<220> FEATURE:
<221> NAME/KEY: MISC_FEATURE
<222> LOCATION: (34)..(34)
<223> OTHER INFORMATION: X= P or S
<220> FEATURE:
<221> NAME/KEY: MISC_FEATURE
<222> LOCATION: (35)..(35)
<223> OTHER INFORMATION: X= A, I or V
<220> FEATURE:
<221> NAME/KEY: MISC_FEATURE
<222> LOCATION: (36)..(36)
<223> OTHER INFORMATION: X= M or W
<220> FEATURE:
<221> NAME/KEY: MISC_FEATURE
<222> LOCATION: (37)..(37)
<223> OTHER INFORMATION: X= G, T or N
```

```
<220> FEATURE:
<221> NAME/KEY: MISC_FEATURE
<222> LOCATION: (38)..(38)
<223> OTHER INFORMATION: X= A, T or L
<220> FEATURE:
<221> NAME/KEY: MISC_FEATURE
<222> LOCATION: (39)..(39)
<223> OTHER INFORMATION: X= A, D or E
<220> FEATURE:
<221> NAME/KEY: MISC_FEATURE
<222> LOCATION: (40)..(40)
<223> OTHER INFORMATION: X= Q, N or S
<220> FEATURE:
<221> NAME/KEY: MISC_FEATURE
<222> LOCATION: (41)..(41)
<223> OTHER INFORMATION: X= W or V
<220> FEATURE:
<221> NAME/KEY: MISC_FEATURE
<222> LOCATION: (42)..(42)
<223> OTHER INFORMATION: X= K or Q
<220> FEATURE:
<221> NAME/KEY: MISC_FEATURE
<222> LOCATION: (43)..(43)
<223> OTHER INFORMATION: X= N, T, K or R
<220> FEATURE:
<221> NAME/KEY: MISC_FEATURE
<222> LOCATION: (44)..(44)
<223> OTHER INFORMATION: X= F or V
<220> FEATURE:
<221> NAME/KEY: MISC_FEATURE
<222> LOCATION: (45)..(45)
<223> OTHER INFORMATION: X= H, S or N
<220> FEATURE:
<221> NAME/KEY: MISC_FEATURE
<222> LOCATION: (46)..(46)
<223> OTHER INFORMATION: X= K, A, T or S
<220> FEATURE:
<221> NAME/KEY: MISC_FEATURE
<222> LOCATION: (48)..(48)
<223> OTHER INFORMATION: X= I, L or V
<220> FEATURE:
<221> NAME/KEY: MISC_FEATURE
<222> LOCATION: (49)..(49)
<223> OTHER INFORMATION: X= I or V
<220> FEATURE:
<221> NAME/KEY: MISC_FEATURE
<222> LOCATION: (50)..(50)
<223> OTHER INFORMATION: X= T or K
<220> FEATURE:
<221> NAME/KEY: MISC_FEATURE
<222> LOCATION: (51)..(51)
<223> OTHER INFORMATION: X= I or L
<220> FEATURE:
<221> NAME/KEY: MISC_FEATURE
<222> LOCATION: (52)..(52)
<223> OTHER INFORMATION: X= V or I
<220> FEATURE:
<221> NAME/KEY: MISC_FEATURE
<222> LOCATION: (53)..(53)
<223> OTHER INFORMATION: X= G or S
<220> FEATURE:
<221> NAME/KEY: MISC_FEATURE
<222> LOCATION: (55)..(55)
<223> OTHER INFORMATION: X= K, S or T
<220> FEATURE:
<221> NAME/KEY: MISC_FEATURE
<222> LOCATION: (56)..(56)
<223> OTHER INFORMATION: X= F or Y
<220> FEATURE:
<221> NAME/KEY: MISC_FEATURE
<222> LOCATION: (57)..(57)
<223> OTHER INFORMATION: X= V, L, F or T
<220> FEATURE:
<221> NAME/KEY: MISC_FEATURE
<222> LOCATION: (58)..(58)
<223> OTHER INFORMATION: X= Q, A, K or S
<220> FEATURE:
<221> NAME/KEY: MISC_FEATURE
<222> LOCATION: (59)..(59)
```

```
<223> OTHER INFORMATION: X= G, K, S or H
<220> FEATURE:
<221> NAME/KEY: MISC_FEATURE
<222> LOCATION: (60)..(60)
<223> OTHER INFORMATION: X= F, Y, T, L or V
<220> FEATURE:
<221> NAME/KEY: MISC_FEATURE
<222> LOCATION: (61)..(61)
<223> OTHER INFORMATION: X=L, T, I or V
<220> FEATURE:
<221> NAME/KEY: MISC_FEATURE
<222> LOCATION: (62)..(62)
<223> OTHER INFORMATION: X=D, N, S, K, G or S
<220> FEATURE:
<221> NAME/KEY: MISC_FEATURE
<222> LOCATION: (63)..(63)
<223> OTHER INFORMATION: X=D, N, R or A
<220> FEATURE:
<221> NAME/KEY: MISC_FEATURE
<222> LOCATION: (64)..(64)
<223> OTHER INFORMATION: X=T or V
<220> FEATURE:
<221> NAME/KEY: MISC_FEATURE
<222> LOCATION: (65)..(65)
<223> OTHER INFORMATION: X=V, L or I
<220> FEATURE:
<221> NAME/KEY: MISC_FEATURE
<222> LOCATION: (66)..(66)
<223> OTHER INFORMATION: X=G or A
<220> FEATURE:
<221> NAME/KEY: MISC_FEATURE
<222> LOCATION: (67)..(67)
<223> OTHER INFORMATION: X=A, Q, V or T
<220> FEATURE:
<221> NAME/KEY: MISC_FEATURE
<222> LOCATION: (68)..(68)
<223> OTHER INFORMATION: X=V, M or L
<220> FEATURE:
<221> NAME/KEY: MISC_FEATURE
<222> LOCATION: (70)..(70)
<223> OTHER INFORMATION: X=S, D or G
<220> FEATURE:
<221> NAME/KEY: MISC_FEATURE
<222> LOCATION: (72)..(72)
<223> OTHER INFORMATION: X=T, N, S or A
<220> FEATURE:
<221> NAME/KEY: MISC_FEATURE
<222> LOCATION: (73)..(73)
<223> OTHER INFORMATION: X=W, Y or T
<220> FEATURE:
<221> NAME/KEY: MISC_FEATURE
<222> LOCATION: (74)..(74)
<223> OTHER INFORMATION: X=T,V or G
<220> FEATURE:
<221> NAME/KEY: MISC_FEATURE
<222> LOCATION: (75)..(75)
<223> OTHER INFORMATION: X=G,W,P,T,K or S
<220> FEATURE:
<221> NAME/KEY: MISC_FEATURE
<222> LOCATION: (76)..(76)
<223> OTHER INFORMATION: X=G,D or K
<220> FEATURE:
<221> NAME/KEY: MISC_FEATURE
<222> LOCATION: (77)..(77)
<223> OTHER INFORMATION: X=G,E, D or V
<220> FEATURE:
<221> NAME/KEY: MISC_FEATURE
<222> LOCATION: (78)..(78)
<223> OTHER INFORMATION: X=G,V, P or D
<220> FEATURE:
<221> NAME/KEY: MISC_FEATURE
<222> LOCATION: (79)..(79)
<223> OTHER INFORMATION: X=M,D,G,L,K or T
<220> FEATURE:
<221> NAME/KEY: MISC_FEATURE
<222> LOCATION: (80)..(80)
<223> OTHER INFORMATION: X=T,G,S,V,N,I or L
<220> FEATURE:
<221> NAME/KEY: MISC_FEATURE
```

```
<222> LOCATION: (81)..(81)
<223> OTHER INFORMATION: X=G,Y,S,A,I or F
<220> FEATURE:
<221> NAME/KEY: MISC_FEATURE
<222> LOCATION: (82)..(82)
<223> OTHER INFORMATION: X=F,S,E or G
<220> FEATURE:
<221> NAME/KEY: MISC_FEATURE
<222> LOCATION: (83)..(83)
<223> OTHER INFORMATION: X=G,V,F,A,K,E or D
<220> FEATURE:
<221> NAME/KEY: MISC_FEATURE
<222> LOCATION: (84)..(84)
<223> OTHER INFORMATION: X=G,K,W,N or E
<220> FEATURE:
<221> NAME/KEY: MISC_FEATURE
<222> LOCATION: (85)..(85)
<223> OTHER INFORMATION: X=Q,N,D,G or L
<220> FEATURE:
<221> NAME/KEY: MISC_FEATURE
<222> LOCATION: (86)..(86)
<223> OTHER INFORMATION: X=F,L,N,Y,F,S or no amino acid
<220> FEATURE:
<221> NAME/KEY: MISC_FEATURE
<222> LOCATION: (87)..(87)
<223> OTHER INFORMATION: X=S,D,G,I or no amino acid
<220> FEATURE:
<221> NAME/KEY: MISC_FEATURE
<222> LOCATION: (88)..(88)
<223> OTHER INFORMATION: X=T,K,S,N or no amino acid
<220> FEATURE:
<221> NAME/KEY: MISC_FEATURE
<222> LOCATION: (89)..(89)
<223> OTHER INFORMATION: X=I,A,L,D,N,Q or no amino acid
<220> FEATURE:
<221> NAME/KEY: MISC_FEATURE
<222> LOCATION: (90)..(90)
<223> OTHER INFORMATION: X=W,Y,S,K,N,T or no amino acid
<220> FEATURE:
<221> NAME/KEY: MISC_FEATURE
<222> LOCATION: (91)..(91)
<223> OTHER INFORMATION: X=K,N,G,V,F; or no amino acid
<220> FEATURE:
<221> NAME/KEY: MISC_FEATURE
<222> LOCATION: (92)..(92)
<223> OTHER INFORMATION: X=K,D,I,F,S or no amino acid
<220> FEATURE:
<221> NAME/KEY: MISC_FEATURE
<222> LOCATION: (93)..(93)
<223> OTHER INFORMATION: X=N,G,V,T or no amino acid
<220> FEATURE:
<221> NAME/KEY: MISC_FEATURE
<222> LOCATION: (94)..(94)
<223> OTHER INFORMATION: X=Y,K,I,L or no amino acid
<220> FEATURE:
<221> NAME/KEY: MISC_FEATURE
<222> LOCATION: (95)..(95)
<223> OTHER INFORMATION: X=T,G,Y,F,W or no amino acid
<220> FEATURE:
<221> NAME/KEY: MISC_FEATURE
<222> LOCATION: (96)..(96)
<223> OTHER INFORMATION: X=D,G,N or no amino acid
<220> FEATURE:
<221> NAME/KEY: MISC_FEATURE
<222> LOCATION: (97)..(97)
<223> OTHER INFORMATION: X=N,K or no amino acid
<220> FEATURE:
<221> NAME/KEY: MISC_FEATURE
<222> LOCATION: (98)..(98)
<223> OTHER INFORMATION: X=V, N or no amino acid
<220> FEATURE:
<221> NAME/KEY: MISC_FEATURE
<222> LOCATION: (99)..(99)
<223> OTHER INFORMATION: X=T,K or no amino acid
<220> FEATURE:
<221> NAME/KEY: MISC_FEATURE
<222> LOCATION: (100)..(100)
<223> OTHER INFORMATION: X=G,D,A or no amino acid
<220> FEATURE:
```

-continued

```
<221> NAME/KEY: MISC_FEATURE
<222> LOCATION: (101)..(101)
<223> OTHER INFORMATION: X=E,L or no amino acid
<220> FEATURE:
<221> NAME/KEY: MISC_FEATURE
<222> LOCATION: (102)..(102)
<223> OTHER INFORMATION: X=S,W or no amino acid
<220> FEATURE:
<221> NAME/KEY: MISC_FEATURE
<222> LOCATION: (103)..(103)
<223> OTHER INFORMATION: X=T,N or no amino acid
<220> FEATURE:
<221> NAME/KEY: MISC_FEATURE
<222> LOCATION: (104)..(104)
<223> OTHER INFORMATION: X=G,F,A,D,V or no amino acid
<220> FEATURE:
<221> NAME/KEY: MISC_FEATURE
<222> LOCATION: (105)..(105)
<223> OTHER INFORMATION: X=A,L,V,D,N,G or no amino acid
<220> FEATURE:
<221> NAME/KEY: MISC_FEATURE
<222> LOCATION: (106)..(106)
<223> OTHER INFORMATION: X=Q,G,I,D,K,H,or R
<220> FEATURE:
<221> NAME/KEY: MISC_FEATURE
<222> LOCATION: (107)..(107)
<223> OTHER INFORMATION: X=K,N,A,P,G,T or L
<220> FEATURE:
<221> NAME/KEY: MISC_FEATURE
<222> LOCATION: (108)..(108)
<223> OTHER INFORMATION: X=F,W,G,N,T or P
<220> FEATURE:
<221> NAME/KEY: MISC_FEATURE
<222> LOCATION: (109)..(109)
<223> OTHER INFORMATION: X=G,P or R
<220> FEATURE:
<221> NAME/KEY: MISC_FEATURE
<222> LOCATION: (110)..(110)
<223> OTHER INFORMATION: X= Y,F,S,D,I,T or G
<220> FEATURE:
<221> NAME/KEY: MISC_FEATURE
<222> LOCATION: (111)..(111)
<223> OTHER INFORMATION: X= G,K,D,E or no amino acid
<220> FEATURE:
<221> NAME/KEY: MISC_FEATURE
<222> LOCATION: (112)..(112)
<223> OTHER INFORMATION: X= A,E,K or D
<220> FEATURE:
<221> NAME/KEY: MISC_FEATURE
<222> LOCATION: (113)..(113)
<223> OTHER INFORMATION: X= L,V,T,N,M or Q
<220> FEATURE:
<221> NAME/KEY: MISC_FEATURE
<222> LOCATION: (114)..(114)
<223> OTHER INFORMATION: X= G,N or T
<220> FEATURE:
<221> NAME/KEY: MISC_FEATURE
<222> LOCATION: (115)..(115)
<223> OTHER INFORMATION: X= V,A,G or F
<220> FEATURE:
<221> NAME/KEY: MISC_FEATURE
<222> LOCATION: (116)..(116)
<223> OTHER INFORMATION: X= V,L,G or F
<220> FEATURE:
<221> NAME/KEY: MISC_FEATURE
<222> LOCATION: (117)..(117)
<223> OTHER INFORMATION: X= N or D
<220> FEATURE:
<221> NAME/KEY: MISC_FEATURE
<222> LOCATION: (118)..(118)
<223> OTHER INFORMATION: X= S,A,K or Y
<220> FEATURE:
<221> NAME/KEY: MISC_FEATURE
<222> LOCATION: (119)..(119)
<223> OTHER INFORMATION: X= I,G,F,A,V or I
<220> FEATURE:
<221> NAME/KEY: MISC_FEATURE
<222> LOCATION: (120)..(120)
<223> OTHER INFORMATION: X= L or M
```

-continued

```
<220> FEATURE:
<221> NAME/KEY: MISC_FEATURE
<222> LOCATION: (121)..(121)
<223> OTHER INFORMATION: X= N,Q or T
<220> FEATURE:
<221> NAME/KEY: MISC_FEATURE
<222> LOCATION: (122)..(122)
<223> OTHER INFORMATION: X= V,I,G,A or T
<220> FEATURE:
<221> NAME/KEY: MISC_FEATURE
<222> LOCATION: (123)..(123)
<223> OTHER INFORMATION: X= A,L,V or I
<220> FEATURE:
<221> NAME/KEY: MISC_FEATURE
<222> LOCATION: (125)..(125)
<223> OTHER INFORMATION: X= N,G,I,M,L or A
<220> FEATURE:
<221> NAME/KEY: MISC_FEATURE
<222> LOCATION: (126)..(126)
<223> OTHER INFORMATION: X= L, G or A
<220> FEATURE:
<221> NAME/KEY: MISC_FEATURE
<222> LOCATION: (127)..(127)
<223> OTHER INFORMATION: X= A or S
<220> FEATURE:
<221> NAME/KEY: MISC_FEATURE
<222> LOCATION: (128)..(128)
<223> OTHER INFORMATION: X= A or V
<220> FEATURE:
<221> NAME/KEY: MISC_FEATURE
<222> LOCATION: (129)..(129)
<223> OTHER INFORMATION: X= I, V or G
<220> FEATURE:
<221> NAME/KEY: MISC_FEATURE
<222> LOCATION: (131)..(131)
<223> OTHER INFORMATION: X= N, Q or T
<220> FEATURE:
<221> NAME/KEY: MISC_FEATURE
<222> LOCATION: (134)..(134)
<223> OTHER INFORMATION: X= F,S,V, or M
<220> FEATURE:
<221> NAME/KEY: MISC_FEATURE
<222> LOCATION: (135)..(135)
<223> OTHER INFORMATION: X= G,S,N,A,T or K
<220> FEATURE:
<221> NAME/KEY: MISC_FEATURE
<222> LOCATION: (136)..(136)
<223> OTHER INFORMATION: X= T,S,E,P or D
<220> FEATURE:
<221> NAME/KEY: MISC_FEATURE
<222> LOCATION: (137)..(137)
<223> OTHER INFORMATION: X= A,I or T
<220> FEATURE:
<221> NAME/KEY: MISC_FEATURE
<222> LOCATION: (138)..(138)
<223> OTHER INFORMATION: X= K, G or A
<220> FEATURE:
<221> NAME/KEY: MISC_FEATURE
<222> LOCATION: (139)..(139)
<223> OTHER INFORMATION: X= N,L,V,K,S or N
<220> FEATURE:
<221> NAME/KEY: MISC_FEATURE
<222> LOCATION: (140)..(140)
<223> OTHER INFORMATION: X= I,E,T,G,L,Y or N
<220> FEATURE:
<221> NAME/KEY: MISC_FEATURE
<222> LOCATION: (141)..(141)
<223> OTHER INFORMATION: X= V, T or F
<220> FEATURE:
<221> NAME/KEY: MISC_FEATURE
<222> LOCATION: (142)..(142)
<223> OTHER INFORMATION: X= G,K,N or A
<220> FEATURE:
<221> NAME/KEY: MISC_FEATURE
<222> LOCATION: (143)..(143)
<223> OTHER INFORMATION: X= E,S,D or K
<220> FEATURE:
<221> NAME/KEY: MISC_FEATURE
<222> LOCATION: (144)..(144)
```

```
<223> OTHER INFORMATION: X= G,V,T or K
<220> FEATURE:
<221> NAME/KEY: MISC_FEATURE
<222> LOCATION: (145)..(145)
<223> OTHER INFORMATION: X= V,T,K,R or E
<220> FEATURE:
<221> NAME/KEY: MISC_FEATURE
<222> LOCATION: (146)..(146)
<223> OTHER INFORMATION: X= Y, L,F, V or T
<220> FEATURE:
<221> NAME/KEY: MISC_FEATURE
<222> LOCATION: (147)..(147)
<223> OTHER INFORMATION: X= K,P,L,D,G or N
<220> FEATURE:
<221> NAME/KEY: MISC_FEATURE
<222> LOCATION: (148)..(148)
<223> OTHER INFORMATION: X= A,T,G,V,F,I or S
<220> FEATURE:
<221> NAME/KEY: MISC_FEATURE
<222> LOCATION: (149)..(149)
<223> OTHER INFORMATION: X= L,T,F,N or no amino acid
<220> FEATURE:
<221> NAME/KEY: MISC_FEATURE
<222> LOCATION: (150)..(150)
<223> OTHER INFORMATION: X= T,G,V or no amino acid
<220> FEATURE:
<221> NAME/KEY: MISC_FEATURE
<222> LOCATION: (151)..(151)
<223> OTHER INFORMATION: X= G,N,K,Q or no amino acid
<220> FEATURE:
<221> NAME/KEY: MISC_FEATURE
<222> LOCATION: (152)..(152)
<223> OTHER INFORMATION: X= K,G,L,V or no amino acid
<220> FEATURE:
<221> NAME/KEY: MISC_FEATURE
<222> LOCATION: (153)..(153)
<223> OTHER INFORMATION: X= I,S,W or no amino acid
<220> FEATURE:
<221> NAME/KEY: MISC_FEATURE
<222> LOCATION: (154)..(154)
<223> OTHER INFORMATION: X= F,G or no amino acid
<220> FEATURE:
<221> NAME/KEY: MISC_FEATURE
<222> LOCATION: (155)..(155)
<223> OTHER INFORMATION: X= D or no amino acid
<220> FEATURE:
<221> NAME/KEY: MISC_FEATURE
<222> LOCATION: (156)..(156)
<223> OTHER INFORMATION: X= L or no amino acid
<220> FEATURE:
<221> NAME/KEY: MISC_FEATURE
<222> LOCATION: (157)..(157)
<223> OTHER INFORMATION: X= P or no amino acid
<220> FEATURE:
<221> NAME/KEY: MISC_FEATURE
<222> LOCATION: (158)..(158)
<223> OTHER INFORMATION: X= N or no amino acid
<220> FEATURE:
<221> NAME/KEY: MISC_FEATURE
<222> LOCATION: (159)..(159)
<223> OTHER INFORMATION: X= N or no amino acid
<220> FEATURE:
<221> NAME/KEY: MISC_FEATURE
<222> LOCATION: (160)..(160)
<223> OTHER INFORMATION: X= G or no amino acid
<220> FEATURE:
<221> NAME/KEY: MISC_FEATURE
<222> LOCATION: (161)..(161)
<223> OTHER INFORMATION: X= G or no amino acid
<220> FEATURE:
<221> NAME/KEY: MISC_FEATURE
<222> LOCATION: (162)..(162)
<223> OTHER INFORMATION: X= S or no amino acid
<220> FEATURE:
<221> NAME/KEY: MISC_FEATURE
<222> LOCATION: (163)..(163)
<223> OTHER INFORMATION: X= G or no amino acid
<220> FEATURE:
<221> NAME/KEY: MISC_FEATURE
```

```
<222> LOCATION: (164)..(164)
<223> OTHER INFORMATION: X= W or no amino acid
<220> FEATURE:
<221> NAME/KEY: MISC_FEATURE
<222> LOCATION: (165)..(165)
<223> OTHER INFORMATION: X= V or no amino acid
<220> FEATURE:
<221> NAME/KEY: MISC_FEATURE
<222> LOCATION: (166)..(166)
<223> OTHER INFORMATION: X= G or no amino acid

<400> SEQUENCE: 1

Met Met Met Pro Ala Asn Xaa Xaa Xaa Xaa Xaa Xaa Xaa Xaa Xaa
1               5                   10                  15

Xaa Val Xaa Gly Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Asn Xaa
        35                  40                  45

Xaa Xaa Xaa Xaa Xaa Asn Xaa Xaa Xaa Xaa Xaa Xaa Xaa Xaa Xaa
    50                  55                  60

Xaa Xaa Xaa Xaa Phe Xaa Gly Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Gly Xaa Xaa Xaa Xaa
        115                 120                 125

Xaa Tyr Xaa Leu Gly Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa
                165

<210> SEQ ID NO 2
<211> LENGTH: 135
<212> TYPE: PRT
<213> ORGANISM: Faecalibacterium prausnitzii

<400> SEQUENCE: 2

Met Met Met Pro Ala Asn Tyr Ser Val Ile Ala Glu Asn Glu Met Thr
1               5                   10                  15

Tyr Val Asn Gly Gly Ala Asn Phe Ile Asp Ala Ile Gly Ala Val Thr
            20                  25                  30

Ala Pro Ile Trp Thr Leu Asp Asn Val Lys Thr Phe Asn Thr Asn Ile
        35                  40                  45

Val Thr Leu Val Gly Asn Thr Phe Leu Gln Ser Thr Ile Asn Arg Thr
    50                  55                  60

Ile Gly Val Leu Phe Ser Gly Asn Thr Thr Trp Lys Glu Val Gly Asn
65                  70                  75                  80

Ile Gly Lys Asn Leu Phe Gly Thr Asn Val Lys Gly Asn Pro Ile Glu
            85                  90                  95

Lys Asn Asn Phe Gly Asp Tyr Ala Met Asn Ala Leu Gly Ile Ala Ala
            100                 105                 110

Ala Val Tyr Asn Leu Gly Val Ala Pro Thr Lys Asn Thr Val Lys Glu
        115                 120                 125

Thr Glu Val Lys Phe Thr Val
```

```
                130                 135
```

<210> SEQ ID NO 3
<211> LENGTH: 143
<212> TYPE: PRT
<213> ORGANISM: Faecalibacterium prausnitzii

<400> SEQUENCE: 3

```
Met Met Met Pro Ala Asn Phe Ser Ala Val Ser Glu Asn Glu Met Thr
1               5                  10                  15

Tyr Val Met Gly Gly Ser Val Ala Asp Tyr Leu Ala Pro Ala Met Gly
            20                  25                  30

Ala Ala Gln Trp Gln Asn Phe His Lys Asn Leu Ile Thr Ile Val Gly
        35                  40                  45

Asn Lys Tyr Val Gln Gly Phe Leu Asp Asn Thr Val Gly Ala Val Phe
    50                  55                  60

Ser Gly Thr Trp Thr Pro Gly Asp Gly Leu Thr Gly Phe Gly Gly Gln
65                  70                  75                  80

Phe Ser Lys Ile Trp Lys Asp Asn Tyr Thr Asp Asn Val Thr Gly Glu
                85                  90                  95

Ser Thr Gly Ala Gln Lys Phe Gly Tyr Gly Ala Leu Gly Val Val Asn
            100                 105                 110

Ser Ile Leu Asn Val Ala Gly Asn Leu Ala Ala Ile Tyr Asn Leu Gly
        115                 120                 125

Phe Gly Thr Ala Lys Asn Ile Val Gly Glu Gly Val Tyr Lys Ala
    130                 135                 140
```

<210> SEQ ID NO 4
<211> LENGTH: 143
<212> TYPE: PRT
<213> ORGANISM: Faecalibacterium prausnitzii

<400> SEQUENCE: 4

```
Met Met Met Pro Ala Asn Phe Ser Ala Val Ser Glu Asn Glu Met Thr
1               5                  10                  15

Tyr Val Met Gly Gly Ser Val Ala Asp Tyr Leu Ala Pro Ala Met Gly
            20                  25                  30

Ala Ala Gln Trp Gln Asn Phe His Lys Asn Leu Ile Thr Ile Val Gly
        35                  40                  45

Asn Lys Tyr Val Gln Gly Phe Leu Asp Asn Thr Val Gly Ala Met Phe
    50                  55                  60

Ser Gly Thr Trp Thr Pro Gly Asp Gly Leu Thr Gly Phe Gly Gly Gln
65                  70                  75                  80

Phe Ser Thr Ile Trp Lys Lys Asn Tyr Thr Asp Asn Val Thr Asp Glu
                85                  90                  95

Ser Thr Gly Ala Gln Lys Phe Gly Tyr Gly Ala Leu Gly Val Val Asn
            100                 105                 110

Ser Ile Leu Asn Val Ala Gly Asn Leu Ala Ala Ile Tyr Asn Leu Gly
        115                 120                 125

Phe Gly Thr Ala Lys Asn Ile Val Gly Glu Gly Val Tyr Lys Ala
    130                 135                 140
```

<210> SEQ ID NO 5
<211> LENGTH: 136
<212> TYPE: PRT
<213> ORGANISM: Faecalibacterium prausnitzii

<400> SEQUENCE: 5

```
Met Met Met Pro Ala Asn Phe Ser Ala Val Ala Glu Asn Glu Met Thr
1               5                   10                  15

Tyr Val Val Gly Gly Ser Leu Val Asp Val Leu Ala Pro Ala Met Thr
                20                  25                  30

Thr Ala Asn Trp Gln Asn Val Ser Ala Asn Val Ile Lys Ile Val Gly
            35                  40                  45

Asn Ser Phe Leu Ala Lys Tyr Thr Asn Asp Val Leu Ala Gln Leu Phe
    50                  55                  60

Asp Gly Asn Tyr Val Pro Gly Asp Val Ile Gly Tyr Ser Val Lys Asn
65                  70                  75                  80

Leu Asp Lys Ala Tyr Asn Lys Gly Tyr Gly Thr Phe Gly Gly Asn Trp
                85                  90                  95

Gly Phe Ala Val Gly Ala Leu Asn Ala Gly Met Gln Ile Leu Gly Gly
                100                 105                 110

Leu Ser Ala Ile Tyr Thr Leu Gly Ser Ser Ile Gly Leu Glu Thr
            115                 120                 125

Lys Ser Gly Thr Leu Pro Thr Leu
        130                 135
```

<210> SEQ ID NO 6
<211> LENGTH: 142
<212> TYPE: PRT
<213> ORGANISM: Faecalibacterium prausnitzii

<400> SEQUENCE: 6

```
Met Met Met Pro Ala Asn Phe Thr Ala Val Asn Ser Glu Val Val Tyr
1               5                   10                  15

Gly Gly Ala Asp Leu Phe Thr Ile Leu Ala Asp Thr Thr Ala Pro Ile
                20                  25                  30

Trp Asn Ala Ala Asn Val Lys Lys Phe Asn Thr Asn Leu Ile Thr Leu
            35                  40                  45

Ile Ser Asn Ser Phe Phe Lys Lys Thr Val Ser Asn Thr Leu Gly Val
    50                  55                  60

Met Phe Gly Gly Asn Trp Gly Lys Asp Gly Asp Lys Ile Phe Gly Glu
65                  70                  75                  80

Glu Gly Ser Ile Asn Gln Asn Val Phe Gly Leu Trp Asn Asp Asp His
                85                  90                  95

Thr Thr Arg Thr Asp Asp Met Thr Phe Gly Asn Lys Val Met Gln Val
                100                 105                 110

Leu Gly Met Ala Ala Val Gly Tyr Thr Leu Gly Thr Thr Asp Ala Lys
            115                 120                 125

Val Gly Phe Asn Asp Gly Val Tyr Gly Ile Asn Gly Lys Leu
        130                 135                 140
```

<210> SEQ ID NO 7
<211> LENGTH: 147
<212> TYPE: PRT
<213> ORGANISM: Faecalibacterium prausnitzii

<400> SEQUENCE: 7

```
Met Met Met Pro Ala Asn Phe Ser Ala Val Asn Ala Glu Val Val Tyr
1               5                   10                  15

Gly Gly Ala Val Ala Asp Tyr Leu Pro Ser Ala Trp Thr Ala Glu Ser
                20                  25                  30

Val Lys Arg Phe Asn Ser Asn Ile Ile Thr Leu Val Ser Asn Ser Phe
            35                  40                  45
```

```
Thr Ser His Leu Leu Lys Ala Thr Leu Gly Thr Met Phe Ser Gly Ser
    50                  55                  60

Trp Gly Ser Asp Gly Val Thr Leu Phe Gly Asp Asn Gly Thr Phe Ser
65                  70                  75                  80

Gly Leu Tyr Asn Val Asn Arg Leu Pro Gly Gly Glu Ala Gln Thr Phe
                85                  90                  95

Gly Asn Lys Ile Met Thr Thr Leu Gly Leu Ala Ser Val Val Tyr Thr
            100                 105                 110

Leu Gly Met Lys Asp Ala Ala Val Leu Thr Ala Lys Lys Val Thr Asn
        115                 120                 125

Ser Asn Gly Gln Val Trp Gly Asp Leu Pro Asn Asn Gly Gly Ser Gly
    130                 135                 140

Trp Val Gly
145

<210> SEQ ID NO 8
<211> LENGTH: 143
<212> TYPE: PRT
<213> ORGANISM: Faecalibacterium prausnitzii

<400> SEQUENCE: 8

Met Met Met Pro Ala Asn Phe Ser Val Val Ala Glu Asn Glu Met Thr
1               5                   10                  15

Tyr Val Val Gly Gly Val Ile Glu Ala Ile Gly Ser Val Thr Ala
            20                  25                  30

Pro Ile Trp Thr Thr Ala Asn Val Lys Thr Phe Asn Thr Asn Leu Val
        35                  40                  45

Thr Ile Ile Gly Asn Ser Tyr Val Ser Lys Leu Val Gly Ala Thr Leu
    50                  55                  60

Gly Val Met Phe Gly Gly Asn Trp Gly Gly Asp Gly Pro Met Ser Ser
65                  70                  75                  80

Phe Phe Gly Asp Asn Gly Ser Leu Ser Gly Ile Val Lys Tyr Gly Ile
                85                  90                  95

Ala Gly Gly Ser Lys Glu Leu Asn Gly Phe Asn Lys Phe Met Gln Val
            100                 105                 110

Val Gly Leu Gly Ala Ala Val Tyr Gln Leu Gly Thr Asn Glu Thr Lys
        115                 120                 125

Lys Tyr Val Lys Glu Val Lys Phe Leu Gly Thr Thr Gly Lys Ile
    130                 135                 140

<210> SEQ ID NO 9
<211> LENGTH: 153
<212> TYPE: PRT
<213> ORGANISM: Faecalibacterium prausnitzii

<400> SEQUENCE: 9

Met Met Met Pro Ala Asn Tyr Ser Ala Ile Ala Glu Asn Glu Met Thr
1               5                   10                  15

Tyr Val Val Gly Gly Leu Leu Glu Ala Ile Gly Ser Val Thr Ala
            20                  25                  30

Pro Val Trp Gly Ala Ala Asn Val Lys Thr Phe Asn Thr Asn Leu Ile
        35                  40                  45

Thr Ile Ile Gly Asn Ser Tyr Val Ser Lys Val Leu Gly Ala Thr Leu
    50                  55                  60

Gly Val Met Phe Ser Gly Ala Trp Gly Thr Lys Asp Asp Val Ala
65                  70                  75                  80
```

Glu Ala Trp Gly Tyr Asp Lys Asp Lys Lys Ile Thr Ile Phe Gly Lys
                85                  90                  95

Asn Lys Ala Leu Trp Asn Ala Leu Asp Pro Asn Gly Asp Lys Glu Thr
            100                 105                 110

Asn Gly Phe Asn Lys Phe Met Gln Gly Ile Gly Ala Leu Ala Ala Val
        115                 120                 125

Tyr Thr Leu Gly Thr Ser Thr Thr Lys Ser Asn Val Ala Glu Gly Arg
    130                 135                 140

Tyr Asp Val Phe Gly Asn Gly Ser Phe
145                 150

<210> SEQ ID NO 10
<211> LENGTH: 143
<212> TYPE: PRT
<213> ORGANISM: Faecalibacterium prausnitzii

<400> SEQUENCE: 10

Met Met Met Pro Ala Asn Phe Ser Ala Val Ser Glu Asn Glu Met Thr
1               5                   10                  15

Tyr Val Met Gly Gly Ser Ile Ala Asp Tyr Leu Ala Pro Ala Met Gly
            20                  25                  30

Ala Ala Gln Trp Gln Asn Phe His Lys Asn Leu Val Thr Ile Val Gly
        35                  40                  45

Asn Lys Tyr Val Gln Gly Phe Leu Asp Asn Thr Val Gly Ala Val Phe
    50                  55                  60

Ser Gly Thr Trp Thr Pro Gly Val Gly Leu Thr Gly Phe Gly Gly Gln
65                  70                  75                  80

Phe Ser Thr Ile Trp Lys Lys Asn Tyr Thr Asp Asn Val Thr Asp Glu
                85                  90                  95

Ser Thr Gly Ala Gln Lys Phe Gly Tyr Gly Ala Leu Gly Val Val Asn
            100                 105                 110

Ser Ile Leu Asn Val Ala Gly Asn Leu Ala Ala Ile Tyr Asn Leu Gly
        115                 120                 125

Phe Gly Thr Ala Lys Asn Ile Val Gly Glu Gly Val Tyr Lys Ala
    130                 135                 140

<210> SEQ ID NO 11
<211> LENGTH: 166
<212> TYPE: PRT
<213> ORGANISM: Artificial Sequence
<220> FEATURE:
<223> OTHER INFORMATION: Consensus sequence
<220> FEATURE:
<221> NAME/KEY: X
<222> LOCATION: (7)..(7)
<223> OTHER INFORMATION: X= Phe or Tyr
<220> FEATURE:
<221> NAME/KEY: X
<222> LOCATION: (8)..(8)
<223> OTHER INFORMATION: X= Ser or Thr
<220> FEATURE:
<221> NAME/KEY: X
<222> LOCATION: (9)..(9)
<223> OTHER INFORMATION: X= Ala or Val
<220> FEATURE:
<221> NAME/KEY: X
<222> LOCATION: (10)..(10)
<223> OTHER INFORMATION: X= Val or Ile
<220> FEATURE:
<221> NAME/KEY: X
<222> LOCATION: (11)..(11)
<223> OTHER INFORMATION: X= Ser, Ala or Asn
<220> FEATURE:

```
<221> NAME/KEY: X
<222> LOCATION: (12)..(12)
<223> OTHER INFORMATION: X= Glu or no amino acid
<220> FEATURE:
<221> NAME/KEY: X
<222> LOCATION: (13)..(13)
<223> OTHER INFORMATION: X= Asn or no amino acid
<220> FEATURE:
<221> NAME/KEY: X
<222> LOCATION: (14)..(14)
<223> OTHER INFORMATION: X= Glu or no amino acid
<220> FEATURE:
<221> NAME/KEY: X
<222> LOCATION: (15)..(15)
<223> OTHER INFORMATION: X= Met, Ser or Ala
<220> FEATURE:
<221> NAME/KEY: X
<222> LOCATION: (16)..(16)
<223> OTHER INFORMATION: X= Thr or Glu
<220> FEATURE:
<221> NAME/KEY: X
<222> LOCATION: (17)..(17)
<223> OTHER INFORMATION: X= Tyr or Val
<220> FEATURE:
<221> NAME/KEY: X
<222> LOCATION: (19)..(19)
<223> OTHER INFORMATION: X= Met, Val, Asn or Tyr
<220> FEATURE:
<221> NAME/KEY: X
<222> LOCATION: (22)..(22)
<223> OTHER INFORMATION: X= Ser or Ala
<220> FEATURE:
<221> NAME/KEY: X
<222> LOCATION: (23)..(23)
<223> OTHER INFORMATION: X= Asn, Asp or no amino acid
<220> FEATURE:
<221> NAME/KEY: X
<222> LOCATION: (24)..(24)
<223> OTHER INFORMATION: X= Phe, Leu or no amino acid
<220> FEATURE:
<221> NAME/KEY: X
<222> LOCATION: (25)..(25)
<223> OTHER INFORMATION: X= Ile, Phe or no amino acid
<220> FEATURE:
<221> NAME/KEY: X
<222> LOCATION: (26)..(26)
<223> OTHER INFORMATION: X= Asp, Thr or no amino acid
<220> FEATURE:
<221> NAME/KEY: X
<222> LOCATION: (27)..(27)
<223> OTHER INFORMATION: X= Ala, Ile or no amino acid
<220> FEATURE:
<221> NAME/KEY: X
<222> LOCATION: (28)..(28)
<223> OTHER INFORMATION: X= Val, Leu or Ile
<220> FEATURE:
<221> NAME/KEY: X
<222> LOCATION: (29)..(29)
<223> OTHER INFORMATION: X= Ala, Val or Gly
<220> FEATURE:
<221> NAME/KEY: X
<222> LOCATION: (30)..(30)
<223> OTHER INFORMATION: X= Ala or Asp
<220> FEATURE:
<221> NAME/KEY: X
<222> LOCATION: (31)..(31)
<223> OTHER INFORMATION: X= Tyr, Val or Thr
<220> FEATURE:
<221> NAME/KEY: X
<222> LOCATION: (32)..(32)
<223> OTHER INFORMATION: X= Leu or Thr
<220> FEATURE:
<221> NAME/KEY: X
<222> LOCATION: (33)..(33)
<223> OTHER INFORMATION: X= Ala or Pro
<220> FEATURE:
<221> NAME/KEY: X
<222> LOCATION: (34)..(34)
<223> OTHER INFORMATION: X= Pro or Ser
```

```
<220> FEATURE:
<221> NAME/KEY: X
<222> LOCATION: (35)..(35)
<223> OTHER INFORMATION: X= Ala or Ile
<220> FEATURE:
<221> NAME/KEY: X
<222> LOCATION: (36)..(36)
<223> OTHER INFORMATION: X= Met or Trp
<220> FEATURE:
<221> NAME/KEY: X
<222> LOCATION: (37)..(37)
<223> OTHER INFORMATION: X= Gly, Thr or Asn
<220> FEATURE:
<221> NAME/KEY: X
<222> LOCATION: (38)..(38)
<223> OTHER INFORMATION: X= Ala, Thr or Leu
<220> FEATURE:
<221> NAME/KEY: X
<222> LOCATION: (39)..(39)
<223> OTHER INFORMATION: X= Ala, Asp or Glu
<220> FEATURE:
<221> NAME/KEY: X
<222> LOCATION: (40)..(40)
<223> OTHER INFORMATION: X= Gln, Asn or Ser
<220> FEATURE:
<221> NAME/KEY: X
<222> LOCATION: (41)..(41)
<223> OTHER INFORMATION: X= Trp or Val
<220> FEATURE:
<221> NAME/KEY: X
<222> LOCATION: (42)..(42)
<223> OTHER INFORMATION: X= Gln or Lys
<220> FEATURE:
<221> NAME/KEY: X
<222> LOCATION: (43)..(43)
<223> OTHER INFORMATION: X= Asn, Thr, Lys or Arg
<220> FEATURE:
<221> NAME/KEY: X
<222> LOCATION: (44)..(44)
<223> OTHER INFORMATION: X= Phe or Val
<220> FEATURE:
<221> NAME/KEY: X
<222> LOCATION: (45)..(45)
<223> OTHER INFORMATION: X= His, Ser, Asn
<220> FEATURE:
<221> NAME/KEY: X
<222> LOCATION: (46)..(46)
<223> OTHER INFORMATION: X= Lys, Ala, Thr or Ser
<220> FEATURE:
<221> NAME/KEY: X
<222> LOCATION: (48)..(48)
<223> OTHER INFORMATION: X= Leu, Val or Ile
<220> FEATURE:
<221> NAME/KEY: X
<222> LOCATION: (49)..(49)
<223> OTHER INFORMATION: X= Ile or Val
<220> FEATURE:
<221> NAME/KEY: X
<222> LOCATION: (50)..(50)
<223> OTHER INFORMATION: X= Thr or Lys
<220> FEATURE:
<221> NAME/KEY: X
<222> LOCATION: (51)..(51)
<223> OTHER INFORMATION: X= Ile or Leu
<220> FEATURE:
<221> NAME/KEY: X
<222> LOCATION: (52)..(52)
<223> OTHER INFORMATION: X= Val or Ile
<220> FEATURE:
<221> NAME/KEY: X
<222> LOCATION: (53)..(53)
<223> OTHER INFORMATION: X= Gly or Ser
<220> FEATURE:
<221> NAME/KEY: X
<222> LOCATION: (55)..(55)
<223> OTHER INFORMATION: X= Lys, Ser or Thr
<220> FEATURE:
<221> NAME/KEY: X
<222> LOCATION: (56)..(56)
```

```
<223> OTHER INFORMATION: X= Tyr or Phe
<220> FEATURE:
<221> NAME/KEY: X
<222> LOCATION: (57)..(57)
<223> OTHER INFORMATION: X= Val, Leu, Phe or Thr
<220> FEATURE:
<221> NAME/KEY: X
<222> LOCATION: (58)..(58)
<223> OTHER INFORMATION: X= Gln, Ala, Lys or Ser
<220> FEATURE:
<221> NAME/KEY: X
<222> LOCATION: (59)..(59)
<223> OTHER INFORMATION: X= Gly, Lys, Ser or His
<220> FEATURE:
<221> NAME/KEY: X
<222> LOCATION: (60)..(60)
<223> OTHER INFORMATION: X= Phe, Tyr, Thr or Leu
<220> FEATURE:
<221> NAME/KEY: X
<222> LOCATION: (61)..(61)
<223> OTHER INFORMATION: X= Leu, Thr, Ile, or Val
<220> FEATURE:
<221> NAME/KEY: X
<222> LOCATION: (62)..(62)
<223> OTHER INFORMATION: X=Asp, Asn, Ser or Lys
<220> FEATURE:
<221> NAME/KEY: X
<222> LOCATION: (63)..(63)
<223> OTHER INFORMATION: X= Asn, Asp, Arg or Ala
<220> FEATURE:
<221> NAME/KEY: X
<222> LOCATION: (64)..(64)
<223> OTHER INFORMATION: X= Thr or Val
<220> FEATURE:
<221> NAME/KEY: X
<222> LOCATION: (65)..(65)
<223> OTHER INFORMATION: X= Val, Leu, Ile
<220> FEATURE:
<221> NAME/KEY: X
<222> LOCATION: (66)..(66)
<223> OTHER INFORMATION: X= Gly or Ala
<220> FEATURE:
<221> NAME/KEY: X
<222> LOCATION: (67)..(67)
<223> OTHER INFORMATION: X= Ala, Gln, Val or Thr
<220> FEATURE:
<221> NAME/KEY: X
<222> LOCATION: (68)..(68)
<223> OTHER INFORMATION: X= Val, Met, Leu
<220> FEATURE:
<221> NAME/KEY: X
<222> LOCATION: (70)..(70)
<223> OTHER INFORMATION: X= Ser, Asp, Gly
<220> FEATURE:
<221> NAME/KEY: X
<222> LOCATION: (72)..(72)
<223> OTHER INFORMATION: X= Thr, Asn, Ser
<220> FEATURE:
<221> NAME/KEY: X
<222> LOCATION: (73)..(73)
<223> OTHER INFORMATION: X= Trp, Tyr or no amino acid
<220> FEATURE:
<221> NAME/KEY: X
<222> LOCATION: (74)..(74)
<223> OTHER INFORMATION: X= Thr, Val or Gly
<220> FEATURE:
<221> NAME/KEY: X
<222> LOCATION: (75)..(75)
<223> OTHER INFORMATION: X= Pro, Thr, Lys or Ser
<220> FEATURE:
<221> NAME/KEY: X
<222> LOCATION: (76)..(76)
<223> OTHER INFORMATION: X= Gly, Trp or Asp
<220> FEATURE:
<221> NAME/KEY: X
<222> LOCATION: (77)..(77)
<223> OTHER INFORMATION: X= Asp, Lys or Gly
<220> FEATURE:
<221> NAME/KEY: X
```

```
<222> LOCATION: (78)..(78)
<223> OTHER INFORMATION: X= Gly, Glu, Asp, Val or no amino acid
<220> FEATURE:
<221> NAME/KEY: X
<222> LOCATION: (79)..(79)
<223> OTHER INFORMATION: X= Leu, Val, Lys or Thr
<220> FEATURE:
<221> NAME/KEY: X
<222> LOCATION: (80)..(80)
<223> OTHER INFORMATION: X= Thr, Ile, Gly or Leu
<220> FEATURE:
<221> NAME/KEY: X
<222> LOCATION: (81)..(81)
<223> OTHER INFORMATION: X= Gly, Asn or Phe
<220> FEATURE:
<221> NAME/KEY: X
<222> LOCATION: (82)..(82)
<223> OTHER INFORMATION: X= Phe, Tyr, Ile or Gly
<220> FEATURE:
<221> NAME/KEY: X
<222> LOCATION: (83)..(83)
<223> OTHER INFORMATION: X= Gly, Ser, Glu or Asp
<220> FEATURE:
<221> NAME/KEY: X
<222> LOCATION: (84)..(84)
<223> OTHER INFORMATION: X= Gly or no amino acid
<220> FEATURE:
<221> NAME/KEY: X
<222> LOCATION: (85)..(85)
<223> OTHER INFORMATION: X= Gln or no amino acid
<220> FEATURE:
<221> NAME/KEY: X
<222> LOCATION: (86)..(86)
<223> OTHER INFORMATION: X= Phe or no amino acid
<220> FEATURE:
<221> NAME/KEY: X
<222> LOCATION: (87)..(87)
<223> OTHER INFORMATION: X= Ser, Val or no amino acid
<220> FEATURE:
<221> NAME/KEY: X
<222> LOCATION: (88)..(88)
<223> OTHER INFORMATION: X= Lys, Thr or no amino acid
<220> FEATURE:
<221> NAME/KEY: X
<222> LOCATION: (89)..(89)
<223> OTHER INFORMATION: X= Ile, Asn or no amino acid
<220> FEATURE:
<221> NAME/KEY: X
<222> LOCATION: (90)..(90)
<223> OTHER INFORMATION: X= Trp, Leu or no amino acid
<220> FEATURE:
<221> NAME/KEY: X
<222> LOCATION: (91)..(91)
<223> OTHER INFORMATION: X= Lys, Asp, Glu or Asn
<220> FEATURE:
<221> NAME/KEY: X
<222> LOCATION: (92)..(92)
<223> OTHER INFORMATION: X= Asp, Lys, Asn or Gly
<220> FEATURE:
<221> NAME/KEY: X
<222> LOCATION: (93)..(93)
<223> OTHER INFORMATION: X= Asn, Ala, Leu, Ser or Thr
<220> FEATURE:
<221> NAME/KEY: X
<222> LOCATION: (94)..(94)
<223> OTHER INFORMATION: X= Tyr, Phe or Ile
<220> FEATURE:
<221> NAME/KEY: X
<222> LOCATION: (95)..(95)
<223> OTHER INFORMATION: X= Thr, Asn, Gly or Ser
<220> FEATURE:
<221> NAME/KEY: X
<222> LOCATION: (96)..(96)
<223> OTHER INFORMATION: X= Asp, Thr, Gln or no amino acid
<220> FEATURE:
<221> NAME/KEY: X
<222> LOCATION: (97)..(97)
<223> OTHER INFORMATION: X= Asn or no amino acid
<220> FEATURE:
```

```
<221> NAME/KEY: X
<222> LOCATION: (98)..(98)
<223> OTHER INFORMATION: X= Val or no amino acid
<220> FEATURE:
<221> NAME/KEY: X
<222> LOCATION: (99)..(99)
<223> OTHER INFORMATION: X= Thr, Lys,Phe or no amino acid
<220> FEATURE:
<221> NAME/KEY: X
<222> LOCATION: (100)..(100)
<223> OTHER INFORMATION: X= Gly or Asp
<220> FEATURE:
<221> NAME/KEY: X
<222> LOCATION: (101)..(101)
<223> OTHER INFORMATION: X= Glu, Tyr, Asn or Leu
<220> FEATURE:
<221> NAME/KEY: X
<222> LOCATION: (102)..(102)
<223> OTHER INFORMATION: X= Ser, Gly, Pro, Trp or Tyr
<220> FEATURE:
<221> NAME/KEY: X
<222> LOCATION: (103)..(103)
<223> OTHER INFORMATION: X= Thr, Ile or Asn
<220> FEATURE:
<221> NAME/KEY: X
<222> LOCATION: (104)..(104)
<223> OTHER INFORMATION: X= Gly, Phe, Glu, Asp or Val
<220> FEATURE:
<221> NAME/KEY: X
<222> LOCATION: (105)..(105)
<223> OTHER INFORMATION: X= Ala, Gly, Lys, Asp or Asn
<220> FEATURE:
<221> NAME/KEY: X
<222> LOCATION: (106)..(106)
<223> OTHER INFORMATION: X= Gln, Gly, Asn, His or Arg
<220> FEATURE:
<221> NAME/KEY: X
<222> LOCATION: (107)..(107)
<223> OTHER INFORMATION: X= Lys, Asn, Thr or Leu
<220> FEATURE:
<221> NAME/KEY: X
<222> LOCATION: (108)..(108)
<223> OTHER INFORMATION: X= Phe, Trp, Thr or Pro
<220> FEATURE:
<221> NAME/KEY: X
<222> LOCATION: (109)..(109)
<223> OTHER INFORMATION: X= Gly or Arg
<220> FEATURE:
<221> NAME/KEY: X
<222> LOCATION: (110)..(110)
<223> OTHER INFORMATION: X= Tyr, Phe, Asp, Thr or Gly
<220> FEATURE:
<221> NAME/KEY: X
<222> LOCATION: (111)..(111)
<223> OTHER INFORMATION: X= Gly, Tyr, Asp, Glu or no amino acid
<220> FEATURE:
<221> NAME/KEY: X
<222> LOCATION: (112)..(112)
<223> OTHER INFORMATION: X= Ala or Asp
<220> FEATURE:
<221> NAME/KEY: X
<222> LOCATION: (113)..(113)
<223> OTHER INFORMATION: X= Leu, Val, Met or Gln
<220> FEATURE:
<221> NAME/KEY: X
<222> LOCATION: (114)..(114)
<223> OTHER INFORMATION: X= Gly, Asn or Thr
<220> FEATURE:
<221> NAME/KEY: X
<222> LOCATION: (115)..(115)
<223> OTHER INFORMATION: X= Val, Ala, or Phe
<220> FEATURE:
<221> NAME/KEY: X
<222> LOCATION: (116)..(116)
<223> OTHER INFORMATION: X= Val or Leu or Gly
<220> FEATURE:
<221> NAME/KEY: X
<222> LOCATION: (117)..(117)
<223> OTHER INFORMATION: X= Asn or no amino acid
```

```
<220> FEATURE:
<221> NAME/KEY: X
<222> LOCATION: (118)..(118)
<223> OTHER INFORMATION: X= Ser, Ala, Lys or no amino acid
<220> FEATURE:
<221> NAME/KEY: X
<222> LOCATION: (119)..(119)
<223> OTHER INFORMATION: X= Ile, Gly, Val or no amino acid
<220> FEATURE:
<221> NAME/KEY: X
<222> LOCATION: (120)..(120)
<223> OTHER INFORMATION: X= Leu, Met or no amino acid
<220> FEATURE:
<221> NAME/KEY: X
<222> LOCATION: (121)..(121)
<223> OTHER INFORMATION: X= Asn, Gln, Thr or no amino acid
<220> FEATURE:
<221> NAME/KEY: X
<222> LOCATION: (122)..(122)
<223> OTHER INFORMATION: X= Val, Ile, Thr or no amino acid
<220> FEATURE:
<221> NAME/KEY: X
<222> LOCATION: (123)..(123)
<223> OTHER INFORMATION: X= Ala, Leu or no amino acid
<220> FEATURE:
<221> NAME/KEY: X
<222> LOCATION: (125)..(125)
<223> OTHER INFORMATION: X= Asn, Gly, Ile, Met or Leu
<220> FEATURE:
<221> NAME/KEY: X
<222> LOCATION: (126)..(126)
<223> OTHER INFORMATION: X= Leu or Ala
<220> FEATURE:
<221> NAME/KEY: X
<222> LOCATION: (127)..(127)
<223> OTHER INFORMATION: X= Ala or Ser
<220> FEATURE:
<221> NAME/KEY: X
<222> LOCATION: (128)..(128)
<223> OTHER INFORMATION: X= Ala or Val
<220> FEATURE:
<221> NAME/KEY: X
<222> LOCATION: (129)..(129)
<223> OTHER INFORMATION: X= Ile, Val or Gly
<220> FEATURE:
<221> NAME/KEY: X
<222> LOCATION: (131)..(131)
<223> OTHER INFORMATION: X= Asn or Thr
<220> FEATURE:
<221> NAME/KEY: X
<222> LOCATION: (134)..(134)
<223> OTHER INFORMATION: X= Phe, Ser, Val, Thr or Met
<220> FEATURE:
<221> NAME/KEY: X
<222> LOCATION: (135)..(135)
<223> OTHER INFORMATION: X= Gly, Ser, Ala, Thr or Lys
<220> FEATURE:
<221> NAME/KEY: X
<222> LOCATION: (136)..(136)
<223> OTHER INFORMATION: X= Thr, Ser, Pro or Asp
<220> FEATURE:
<221> NAME/KEY: X
<222> LOCATION: (137)..(137)
<223> OTHER INFORMATION: X= Ala, Ile or Thr
<220> FEATURE:
<221> NAME/KEY: X
<222> LOCATION: (138)..(138)
<223> OTHER INFORMATION: X= Lys, Gly or Ala
<220> FEATURE:
<221> NAME/KEY: X
<222> LOCATION: (139)..(139)
<223> OTHER INFORMATION: X= Asn, Leu or Val
<220> FEATURE:
<221> NAME/KEY: X
<222> LOCATION: (140)..(140)
<223> OTHER INFORMATION: X= Ile, Glu, Thr, Gly or Leu
<220> FEATURE:
<221> NAME/KEY: X
<222> LOCATION: (141)..(141)
```

-continued

```
<223> OTHER INFORMATION: X= Val, Thr or Phe
<220> FEATURE:
<221> NAME/KEY: X
<222> LOCATION: (142)..(142)
<223> OTHER INFORMATION: X= Gly, Lys, Asn or Ala
<220> FEATURE:
<221> NAME/KEY: X
<222> LOCATION: (143)..(143)
<223> OTHER INFORMATION: X= Glu, Ser, Asp or Lys
<220> FEATURE:
<221> NAME/KEY: X
<222> LOCATION: (144)..(144)
<223> OTHER INFORMATION: X= Gly, Thr, Lys
<220> FEATURE:
<221> NAME/KEY: X
<222> LOCATION: (145)..(145)
<223> OTHER INFORMATION: X= Val, Thr or Glu
<220> FEATURE:
<221> NAME/KEY: X
<222> LOCATION: (146)..(146)
<223> OTHER INFORMATION: X= Tyr, Leu, Val or Thr
<220> FEATURE:
<221> NAME/KEY: X
<222> LOCATION: (147)..(147)
<223> OTHER INFORMATION: X= Lys, Pro, Gly or Asn
<220> FEATURE:
<221> NAME/KEY: X
<222> LOCATION: (148)..(148)
<223> OTHER INFORMATION: X= Ala, Thr, Phe, Ile or Ser
<220> FEATURE:
<221> NAME/KEY: X
<222> LOCATION: (149)..(149)
<223> OTHER INFORMATION: X= Leu, Thr, Asn or no amino acid
<220> FEATURE:
<221> NAME/KEY: X
<222> LOCATION: (150)..(150)
<223> OTHER INFORMATION: X= Val, Gly or no amino acid
<220> FEATURE:
<221> NAME/KEY: X
<222> LOCATION: (151)..(151)
<223> OTHER INFORMATION: X= Lys, Gln or no amino acid
<220> FEATURE:
<221> NAME/KEY: X
<222> LOCATION: (152)..(152)
<223> OTHER INFORMATION: X= Leu, Val or no amino acid
<220> FEATURE:
<221> NAME/KEY: X
<222> LOCATION: (153)..(153)
<223> OTHER INFORMATION: X= Trp or no amino acid
<220> FEATURE:
<221> NAME/KEY: X
<222> LOCATION: (154)..(154)
<223> OTHER INFORMATION: X= Gly or no amino acid
<220> FEATURE:
<221> NAME/KEY: X
<222> LOCATION: (155)..(155)
<223> OTHER INFORMATION: X= Asp or no amino acid
<220> FEATURE:
<221> NAME/KEY: X
<222> LOCATION: (156)..(156)
<223> OTHER INFORMATION: X= Leu or no amino acid
<220> FEATURE:
<221> NAME/KEY: X
<222> LOCATION: (157)..(157)
<223> OTHER INFORMATION: X= Pro or no amino acid
<220> FEATURE:
<221> NAME/KEY: X
<222> LOCATION: (158)..(158)
<223> OTHER INFORMATION: X= Asn or no amino acid
<220> FEATURE:
<221> NAME/KEY: X
<222> LOCATION: (159)..(159)
<223> OTHER INFORMATION: X= Asn or no amino acid
<220> FEATURE:
<221> NAME/KEY: X
<222> LOCATION: (160)..(160)
<223> OTHER INFORMATION: X= Gly or no amino acid
<220> FEATURE:
<221> NAME/KEY: X
```

```
<222> LOCATION: (161)..(161)
<223> OTHER INFORMATION: X= Gly or no amino acid
<220> FEATURE:
<221> NAME/KEY: X
<222> LOCATION: (162)..(162)
<223> OTHER INFORMATION: X= Ser or no amino acid
<220> FEATURE:
<221> NAME/KEY: X
<222> LOCATION: (163)..(163)
<223> OTHER INFORMATION: X= Gly or no amino acid
<220> FEATURE:
<221> NAME/KEY: X
<222> LOCATION: (164)..(164)
<223> OTHER INFORMATION: X= Trp or no amino acid
<220> FEATURE:
<221> NAME/KEY: X
<222> LOCATION: (165)..(165)
<223> OTHER INFORMATION: X= Val or no amino acid
<220> FEATURE:
<221> NAME/KEY: X
<222> LOCATION: (166)..(166)
<223> OTHER INFORMATION: X= Gly or no amino acid

<400> SEQUENCE: 11

Met Met Met Pro Ala Asn Xaa Xaa Xaa Xaa Xaa Xaa Xaa Xaa Xaa
1               5                   10                  15

Xaa Val Xaa Gly Gly Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Asn Xaa
        35                  40                  45

Xaa Xaa Xaa Xaa Xaa Asn Xaa Xaa Xaa Xaa Xaa Xaa Xaa Xaa Xaa
    50                  55                  60

Xaa Xaa Xaa Xaa Phe Xaa Gly Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Gly Xaa Xaa Xaa Xaa
        115                 120                 125

Xaa Tyr Xaa Leu Gly Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa
                165

<210> SEQ ID NO 12
<211> LENGTH: 20
<212> TYPE: PRT
<213> ORGANISM: Artificial Sequence
<220> FEATURE:
<223> OTHER INFORMATION: p49-70 portion of SEQ ID NO:2

<400> SEQUENCE: 12

Val Thr Leu Val Gly Asn Thr Phe Leu Gln Ser Thr Ile Asn Arg Thr
1               5                   10                  15

Ile Gly Val Leu
            20

<210> SEQ ID NO 13
<211> LENGTH: 43
<212> TYPE: PRT
<213> ORGANISM: Artificial Sequence
```

```
<220> FEATURE:
<223> OTHER INFORMATION: p35-77 portion of SEQ ID NO:2

<400> SEQUENCE: 13

Ile Trp Thr Leu Asp Asn Val Lys Thr Phe Asn Thr Asn Ile Val Thr
1               5                   10                  15

Leu Val Gly Asn Thr Phe Leu Gln Ser Thr Ile Asn Arg Thr Ile Gly
            20                  25                  30

Val Leu Phe Ser Gly Asn Thr Thr Trp Lys Glu
            35                  40

<210> SEQ ID NO 14
<211> LENGTH: 20
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: X= I or V
<220> FEATURE:
<221> NAME/KEY: MISC_FEATURE
<222> LOCATION: (2)..(2)
<223> OTHER INFORMATION: X= T or K
<220> FEATURE:
<221> NAME/KEY: MISC_FEATURE
<222> LOCATION: (3)..(3)
<223> OTHER INFORMATION: X= I or L
<220> FEATURE:
<221> NAME/KEY: MISC_FEATURE
<222> LOCATION: (4)..(4)
<223> OTHER INFORMATION: X= V or I
<220> FEATURE:
<221> NAME/KEY: MISC_FEATURE
<222> LOCATION: (5)..(5)
<223> OTHER INFORMATION: X= G or S
<220> FEATURE:
<221> NAME/KEY: MISC_FEATURE
<222> LOCATION: (7)..(7)
<223> OTHER INFORMATION: X= K, S or T
<220> FEATURE:
<221> NAME/KEY: MISC_FEATURE
<222> LOCATION: (8)..(8)
<223> OTHER INFORMATION: X= Y or F
<220> FEATURE:
<221> NAME/KEY: MISC_FEATURE
<222> LOCATION: (9)..(9)
<223> OTHER INFORMATION: X= V,L,F or T
<220> FEATURE:
<221> NAME/KEY: MISC_FEATURE
<222> LOCATION: (10)..(10)
<223> OTHER INFORMATION: X= Q,A,K or S
<220> FEATURE:
<221> NAME/KEY: MISC_FEATURE
<222> LOCATION: (11)..(11)
<223> OTHER INFORMATION: X= G,K,S or H
<220> FEATURE:
<221> NAME/KEY: MISC_FEATURE
<222> LOCATION: (12)..(12)
<223> OTHER INFORMATION: X= F,Y,T or L
<220> FEATURE:
<221> NAME/KEY: MISC_FEATURE
<222> LOCATION: (13)..(13)
<223> OTHER INFORMATION: X= L,T,I or V
<220> FEATURE:
<221> NAME/KEY: MISC_FEATURE
<222> LOCATION: (14)..(14)
<223> OTHER INFORMATION: X= D,N,S or K
<220> FEATURE:
<221> NAME/KEY: MISC_FEATURE
<222> LOCATION: (15)..(15)
<223> OTHER INFORMATION: X= N,D,R or A
<220> FEATURE:
<221> NAME/KEY: MISC_FEATURE
```

```
<222> LOCATION: (16)..(16)
<223> OTHER INFORMATION: X= T or V
<220> FEATURE:
<221> NAME/KEY: MISC_FEATURE
<222> LOCATION: (17)..(17)
<223> OTHER INFORMATION: X= V,L or I
<220> FEATURE:
<221> NAME/KEY: MISC_FEATURE
<222> LOCATION: (18)..(18)
<223> OTHER INFORMATION: X= G or A
<220> FEATURE:
<221> NAME/KEY: MISC_FEATURE
<222> LOCATION: (19)..(19)
<223> OTHER INFORMATION: X=A,Q,V or T
<220> FEATURE:
<221> NAME/KEY: MISC_FEATURE
<222> LOCATION: (20)..(20)
<223> OTHER INFORMATION: X=V,M or L

<400> SEQUENCE: 14

Xaa Xaa Xaa Xaa Xaa Asn Xaa Xaa Xaa Xaa Xaa Xaa Xaa Xaa Xaa
1               5                   10                  15

Xaa Xaa Xaa Xaa
            20

<210> SEQ ID NO 15
<211> LENGTH: 20
<212> TYPE: PRT
<213> ORGANISM: Artificial Sequence
<220> FEATURE:
<223> OTHER INFORMATION: SL3/3 fragment

<400> SEQUENCE: 15

Ile Thr Ile Val Gly Asn Lys Tyr Val Gln Gly Phe Leu Asp Asn Thr
1               5                   10                  15

Val Gly Ala Val
            20

<210> SEQ ID NO 16
<211> LENGTH: 20
<212> TYPE: PRT
<213> ORGANISM: Artificial Sequence
<220> FEATURE:
<223> OTHER INFORMATION: M21/2 fragment

<400> SEQUENCE: 16

Ile Thr Ile Val Gly Asn Lys Tyr Val Gln Gly Phe Leu Asp Asn Thr
1               5                   10                  15

Val Gly Ala Met
            20

<210> SEQ ID NO 17
<211> LENGTH: 20
<212> TYPE: PRT
<213> ORGANISM: Artificial Sequence
<220> FEATURE:
<223> OTHER INFORMATION: KLE1255 fragment

<400> SEQUENCE: 17

Ile Lys Ile Val Gly Asn Ser Phe Leu Ala Lys Tyr Thr Asn Asp Val
1               5                   10                  15

Leu Ala Gln Leu
            20

<210> SEQ ID NO 18
<211> LENGTH: 20
<212> TYPE: PRT
```

<213> ORGANISM: Artificial Sequence
<220> FEATURE:
<223> OTHER INFORMATION: L2-61 fragment

<400> SEQUENCE: 18

Ile Thr Leu Ile Ser Asn Ser Phe Phe Lys Lys Thr Val Ser Asn Thr
1               5                   10                  15

Leu Gly Val Met
            20

<210> SEQ ID NO 19
<211> LENGTH: 20
<212> TYPE: PRT
<213> ORGANISM: Artificial Sequence
<220> FEATURE:
<223> OTHER INFORMATION: L2-62 fragment

<400> SEQUENCE: 19

Ile Thr Leu Val Ser Asn Ser Phe Thr Ser His Leu Leu Lys Ala Thr
1               5                   10                  15

Leu Gly Thr Met
            20

<210> SEQ ID NO 20
<211> LENGTH: 20
<212> TYPE: PRT
<213> ORGANISM: Artificial Sequence
<220> FEATURE:
<223> OTHER INFORMATION: CAG821 fragment

<400> SEQUENCE: 20

Val Thr Ile Ile Gly Asn Ser Tyr Val Ser Lys Leu Val Gly Ala Thr
1               5                   10                  15

Leu Gly Val Met
            20

<210> SEQ ID NO 21
<211> LENGTH: 20
<212> TYPE: PRT
<213> ORGANISM: Artificial Sequence
<220> FEATURE:
<223> OTHER INFORMATION: CAG822 fragment

<400> SEQUENCE: 21

Ile Thr Ile Ile Gly Asn Ser Tyr Val Ser Lys Val Leu Gly Ala Thr
1               5                   10                  15

Leu Gly Val Met
            20

<210> SEQ ID NO 22
<211> LENGTH: 18
<212> TYPE: PRT
<213> ORGANISM: Artificial Sequence
<220> FEATURE:
<223> OTHER INFORMATION: CNCM-4573 fragment

<400> SEQUENCE: 22

Ile Val Gly Asn Lys Tyr Val Gln Gly Phe Leu Asp Asn Thr Val Gly
1               5                   10                  15

Ala Val

<210> SEQ ID NO 23
<211> LENGTH: 43
<212> TYPE: PRT

```
<213> ORGANISM: Artificial Sequence
<220> FEATURE:
<223> OTHER INFORMATION: consensus p35-77
<220> FEATURE:
<221> NAME/KEY: MISC_FEATURE
<222> LOCATION: (1)..(1)
<223> OTHER INFORMATION: X=A,I or V
<220> FEATURE:
<221> NAME/KEY: MISC_FEATURE
<222> LOCATION: (2)..(2)
<223> OTHER INFORMATION: X=M or W
<220> FEATURE:
<221> NAME/KEY: MISC_FEATURE
<222> LOCATION: (3)..(3)
<223> OTHER INFORMATION: X=G, T or N
<220> FEATURE:
<221> NAME/KEY: MISC_FEATURE
<222> LOCATION: (4)..(4)
<223> OTHER INFORMATION: X=A, T or L
<220> FEATURE:
<221> NAME/KEY: MISC_FEATURE
<222> LOCATION: (5)..(5)
<223> OTHER INFORMATION: X=A, D or E
<220> FEATURE:
<221> NAME/KEY: MISC_FEATURE
<222> LOCATION: (6)..(6)
<223> OTHER INFORMATION: X=Q, N or S
<220> FEATURE:
<221> NAME/KEY: MISC_FEATURE
<222> LOCATION: (7)..(7)
<223> OTHER INFORMATION: X=W or V
<220> FEATURE:
<221> NAME/KEY: MISC_FEATURE
<222> LOCATION: (8)..(8)
<223> OTHER INFORMATION: X=Q or K
<220> FEATURE:
<221> NAME/KEY: MISC_FEATURE
<222> LOCATION: (9)..(9)
<223> OTHER INFORMATION: X=N,T,K or R
<220> FEATURE:
<221> NAME/KEY: MISC_FEATURE
<222> LOCATION: (10)..(10)
<223> OTHER INFORMATION: X=F or V
<220> FEATURE:
<221> NAME/KEY: MISC_FEATURE
<222> LOCATION: (11)..(11)
<223> OTHER INFORMATION: X=H,S or N
<220> FEATURE:
<221> NAME/KEY: MISC_FEATURE
<222> LOCATION: (12)..(12)
<223> OTHER INFORMATION: X=K,A,T or S
<220> FEATURE:
<221> NAME/KEY: MISC_FEATURE
<222> LOCATION: (14)..(14)
<223> OTHER INFORMATION: X=L,V or I
<220> FEATURE:
<221> NAME/KEY: MISC_FEATURE
<222> LOCATION: (15)..(15)
<223> OTHER INFORMATION: X=V or I
<220> FEATURE:
<221> NAME/KEY: MISC_FEATURE
<222> LOCATION: (16)..(16)
<223> OTHER INFORMATION: X=T or K
<220> FEATURE:
<221> NAME/KEY: MISC_FEATURE
<222> LOCATION: (17)..(17)
<223> OTHER INFORMATION: X=I or L
<220> FEATURE:
<221> NAME/KEY: MISC_FEATURE
<222> LOCATION: (18)..(18)
<223> OTHER INFORMATION: X=V or I
<220> FEATURE:
<221> NAME/KEY: MISC_FEATURE
<222> LOCATION: (19)..(19)
<223> OTHER INFORMATION: X=G or S
<220> FEATURE:
<221> NAME/KEY: MISC_FEATURE
<222> LOCATION: (21)..(21)
<223> OTHER INFORMATION: X=K,T or S
```

```
<220> FEATURE:
<221> NAME/KEY: MISC_FEATURE
<222> LOCATION: (22)..(22)
<223> OTHER INFORMATION: X=Y or F
<220> FEATURE:
<221> NAME/KEY: MISC_FEATURE
<222> LOCATION: (23)..(23)
<223> OTHER INFORMATION: X=V,L,F or T
<220> FEATURE:
<221> NAME/KEY: MISC_FEATURE
<222> LOCATION: (24)..(24)
<223> OTHER INFORMATION: XQ,A,K or S
<220> FEATURE:
<221> NAME/KEY: MISC_FEATURE
<222> LOCATION: (25)..(25)
<223> OTHER INFORMATION: XQ,A,K or S
<220> FEATURE:
<221> NAME/KEY: MISC_FEATURE
<222> LOCATION: (25)..(25)
<223> OTHER INFORMATION: X=G,K,S or H
<220> FEATURE:
<221> NAME/KEY: MISC_FEATURE
<222> LOCATION: (26)..(26)
<223> OTHER INFORMATION: X=F,Y,T or L
<220> FEATURE:
<221> NAME/KEY: MISC_FEATURE
<222> LOCATION: (27)..(27)
<223> OTHER INFORMATION: X=L,T,I or V
<220> FEATURE:
<221> NAME/KEY: MISC_FEATURE
<222> LOCATION: (28)..(28)
<223> OTHER INFORMATION: X=D,N,S or K
<220> FEATURE:
<221> NAME/KEY: MISC_FEATURE
<222> LOCATION: (29)..(29)
<223> OTHER INFORMATION: X=N,D,R or A
<220> FEATURE:
<221> NAME/KEY: MISC_FEATURE
<222> LOCATION: (30)..(30)
<223> OTHER INFORMATION: X=T or V
<220> FEATURE:
<221> NAME/KEY: MISC_FEATURE
<222> LOCATION: (31)..(31)
<223> OTHER INFORMATION: X=V,L or I
<220> FEATURE:
<221> NAME/KEY: MISC_FEATURE
<222> LOCATION: (32)..(32)
<223> OTHER INFORMATION: X=G or A
<220> FEATURE:
<221> NAME/KEY: MISC_FEATURE
<222> LOCATION: (33)..(33)
<223> OTHER INFORMATION: X=A,Q,V or T
<220> FEATURE:
<221> NAME/KEY: MISC_FEATURE
<222> LOCATION: (34)..(34)
<223> OTHER INFORMATION: X=V,M or L
<220> FEATURE:
<221> NAME/KEY: MISC_FEATURE
<222> LOCATION: (36)..(36)
<223> OTHER INFORMATION: X=S,D or G
<220> FEATURE:
<221> NAME/KEY: MISC_FEATURE
<222> LOCATION: (38)..(38)
<223> OTHER INFORMATION: X=T,N,S or A
<220> FEATURE:
<221> NAME/KEY: MISC_FEATURE
<222> LOCATION: (39)..(39)
<223> OTHER INFORMATION: X=W,Y,Tor no amino acid
<220> FEATURE:
<221> NAME/KEY: MISC_FEATURE
<222> LOCATION: (40)..(40)
<223> OTHER INFORMATION: X=T,V  or G
<220> FEATURE:
<221> NAME/KEY: MISC_FEATURE
<222> LOCATION: (41)..(41)
<223> OTHER INFORMATION: X=G,W,P,T,K or S
<220> FEATURE:
<221> NAME/KEY: MISC_FEATURE
<222> LOCATION: (42)..(42)
```

<223> OTHER INFORMATION: X=G,K or D
<220> FEATURE:
<221> NAME/KEY: MISC_FEATURE
<222> LOCATION: (43)..(43)
<223> OTHER INFORMATION: X=G,E,D or V

<400> SEQUENCE: 23

Xaa Xaa Xaa Xaa Xaa Xaa Xaa Xaa Xaa Xaa Xaa Asn Xaa Xaa Xaa
1               5                   10                  15

Xaa Xaa Xaa Asn Xaa Xaa Xaa Xaa Xaa Xaa Xaa Xaa Xaa Xaa Xaa
            20                  25                  30

Xaa Xaa Phe Xaa Gly Xaa Xaa Xaa Xaa Xaa Xaa
        35                  40

<210> SEQ ID NO 24
<211> LENGTH: 43
<212> TYPE: PRT
<213> ORGANISM: Artificial Sequence
<220> FEATURE:
<223> OTHER INFORMATION: SL3/3 fragment

<400> SEQUENCE: 24

Ala Met Gly Ala Ala Gln Trp Gln Asn Phe His Lys Asn Leu Ile Thr
1               5                   10                  15

Ile Val Gly Asn Lys Tyr Val Gln Gly Phe Leu Asp Asn Thr Val Gly
            20                  25                  30

Ala Val Phe Ser Gly Thr Trp Thr Pro Gly Asp
        35                  40

<210> SEQ ID NO 25
<211> LENGTH: 43
<212> TYPE: PRT
<213> ORGANISM: Artificial Sequence
<220> FEATURE:
<223> OTHER INFORMATION: M21/2 fragment

<400> SEQUENCE: 25

Ala Met Gly Ala Ala Gln Trp Gln Asn Phe His Lys Asn Leu Ile Thr
1               5                   10                  15

Ile Val Gly Asn Lys Tyr Val Gln Gly Phe Leu Asp Asn Thr Val Gly
            20                  25                  30

Ala Met Phe Ser Gly Thr Trp Thr Pro Gly Asp
        35                  40

<210> SEQ ID NO 26
<211> LENGTH: 43
<212> TYPE: PRT
<213> ORGANISM: Artificial Sequence
<220> FEATURE:
<223> OTHER INFORMATION: KLE1255 fragment

<400> SEQUENCE: 26

Ala Met Thr Thr Ala Asn Trp Gln Asn Val Ser Ala Asn Val Ile Lys
1               5                   10                  15

Ile Val Gly Asn Ser Phe Leu Ala Lys Tyr Thr Asn Asp Val Leu Ala
            20                  25                  30

Gln Leu Phe Asp Gly Asn Tyr Val Pro Gly Asp
        35                  40

<210> SEQ ID NO 27
<211> LENGTH: 43
<212> TYPE: PRT
<213> ORGANISM: Artificial Sequence

```
<220> FEATURE:
<223> OTHER INFORMATION: L2-61 fragment

<400> SEQUENCE: 27

Ile Trp Asn Ala Ala Asn Val Lys Lys Phe Asn Thr Asn Leu Ile Thr
1               5                   10                  15

Leu Ile Ser Asn Ser Phe Phe Lys Lys Thr Val Ser Asn Thr Leu Gly
            20                  25                  30

Val Met Phe Gly Gly Asn Trp Gly Lys Asp Gly
        35                  40

<210> SEQ ID NO 28
<211> LENGTH: 43
<212> TYPE: PRT
<213> ORGANISM: Artificial Sequence
<220> FEATURE:
<223> OTHER INFORMATION: L2-62 fragment

<400> SEQUENCE: 28

Ala Trp Thr Ala Glu Ser Val Lys Arg Phe Asn Ser Asn Ile Ile Thr
1               5                   10                  15

Leu Val Ser Asn Ser Phe Thr Ser His Leu Leu Lys Ala Thr Leu Gly
            20                  25                  30

Thr Met Phe Ser Gly Ser Trp Gly Ser Asp Gly
        35                  40

<210> SEQ ID NO 29
<211> LENGTH: 43
<212> TYPE: PRT
<213> ORGANISM: Artificial Sequence
<220> FEATURE:
<223> OTHER INFORMATION: CAG:821 fragment

<400> SEQUENCE: 29

Ile Trp Thr Thr Ala Asn Val Lys Thr Phe Asn Thr Asn Leu Val Thr
1               5                   10                  15

Ile Ile Gly Asn Ser Tyr Val Ser Lys Leu Val Gly Ala Thr Leu Gly
            20                  25                  30

Val Met Phe Gly Gly Asn Trp Gly Gly Asp Gly
        35                  40

<210> SEQ ID NO 30
<211> LENGTH: 43
<212> TYPE: PRT
<213> ORGANISM: Artificial Sequence
<220> FEATURE:
<223> OTHER INFORMATION: CAG:822 fragment

<400> SEQUENCE: 30

Val Trp Gly Ala Ala Asn Val Lys Thr Phe Asn Thr Asn Leu Ile Thr
1               5                   10                  15

Ile Ile Gly Asn Ser Tyr Val Ser Lys Val Leu Gly Ala Thr Leu Gly
            20                  25                  30

Val Met Phe Ser Gly Ala Trp Gly Thr Lys Asp
        35                  40

<210> SEQ ID NO 31
<211> LENGTH: 43
<212> TYPE: PRT
<213> ORGANISM: Artificial Sequence
<220> FEATURE:
<223> OTHER INFORMATION: CNCM-4573 fragment
```

<400> SEQUENCE: 31

Ala Met Gly Ala Ala Gln Trp Gln Asn Phe His Lys Asn Leu Val Thr
1               5                   10                  15

Ile Val Gly Asn Lys Tyr Val Gln Gly Phe Leu Asp Asn Thr Val Gly
                20                  25                  30

Ala Val Phe Ser Gly Thr Trp Thr Pro Gly Val
                35                  40

<210> SEQ ID NO 32
<211> LENGTH: 71
<212> TYPE: PRT
<213> ORGANISM: Artificial Sequence
<220> FEATURE:
<223> OTHER INFORMATION: consensus sequence
<220> FEATURE:
<221> NAME/KEY: X
<222> LOCATION: (7)..(7)
<223> OTHER INFORMATION: X= Phe or Tyr
<220> FEATURE:
<221> NAME/KEY: X
<222> LOCATION: (8)..(8)
<223> OTHER INFORMATION: X= Ser or Thr
<220> FEATURE:
<221> NAME/KEY: X
<222> LOCATION: (9)..(9)
<223> OTHER INFORMATION: X= Ala or Val
<220> FEATURE:
<221> NAME/KEY: X
<222> LOCATION: (10)..(10)
<223> OTHER INFORMATION: X= Val or Ile
<220> FEATURE:
<221> NAME/KEY: X
<222> LOCATION: (11)..(11)
<223> OTHER INFORMATION: X= Ser, Ala or Asn
<220> FEATURE:
<221> NAME/KEY: X
<222> LOCATION: (12)..(12)
<223> OTHER INFORMATION: X= Glu or no amino acid
<220> FEATURE:
<221> NAME/KEY: X
<222> LOCATION: (13)..(13)
<223> OTHER INFORMATION: X= Asn or no amino acid
<220> FEATURE:
<221> NAME/KEY: X
<222> LOCATION: (14)..(14)
<223> OTHER INFORMATION: X= Glu or no amino acid
<220> FEATURE:
<221> NAME/KEY: X
<222> LOCATION: (15)..(15)
<223> OTHER INFORMATION: X= Met, Ser or Ala
<220> FEATURE:
<221> NAME/KEY: X
<222> LOCATION: (16)..(16)
<223> OTHER INFORMATION: X= Thr or Glu
<220> FEATURE:
<221> NAME/KEY: X
<222> LOCATION: (17)..(17)
<223> OTHER INFORMATION: X= Tyr or Val
<220> FEATURE:
<221> NAME/KEY: X
<222> LOCATION: (19)..(19)
<223> OTHER INFORMATION: X= Met, Val, Asn or Tyr
<220> FEATURE:
<221> NAME/KEY: X
<222> LOCATION: (22)..(22)
<223> OTHER INFORMATION: X= Ser or Ala
<220> FEATURE:
<221> NAME/KEY: X
<222> LOCATION: (23)..(23)
<223> OTHER INFORMATION: X= Asn, Asp or no amino acid
<220> FEATURE:
<221> NAME/KEY: X
<222> LOCATION: (24)..(24)
<223> OTHER INFORMATION: X= Phe, Leu or no amino acid
<220> FEATURE:

```
<221> NAME/KEY: X
<222> LOCATION: (25)..(25)
<223> OTHER INFORMATION: X= Ile, Phe or no amino acid
<220> FEATURE:
<221> NAME/KEY: X
<222> LOCATION: (26)..(26)
<223> OTHER INFORMATION: X= Asp, Thr or no amino acid
<220> FEATURE:
<221> NAME/KEY: X
<222> LOCATION: (27)..(27)
<223> OTHER INFORMATION: X= Ala, Ile or no amino acid
<220> FEATURE:
<221> NAME/KEY: X
<222> LOCATION: (28)..(28)
<223> OTHER INFORMATION: X= Val, Leu or Ile
<220> FEATURE:
<221> NAME/KEY: X
<222> LOCATION: (29)..(29)
<223> OTHER INFORMATION: X= Ala, Val or Gly
<220> FEATURE:
<221> NAME/KEY: X
<222> LOCATION: (30)..(30)
<223> OTHER INFORMATION: X= Ala or Asp
<220> FEATURE:
<221> NAME/KEY: X
<222> LOCATION: (31)..(31)
<223> OTHER INFORMATION: X= Tyr, Val or Thr
<220> FEATURE:
<221> NAME/KEY: X
<222> LOCATION: (32)..(32)
<223> OTHER INFORMATION: X= Leu or Thr
<220> FEATURE:
<221> NAME/KEY: X
<222> LOCATION: (33)..(33)
<223> OTHER INFORMATION: X= Ala or Pro
<220> FEATURE:
<221> NAME/KEY: X
<222> LOCATION: (34)..(34)
<223> OTHER INFORMATION: X= Pro or Ser
<220> FEATURE:
<221> NAME/KEY: X
<222> LOCATION: (35)..(35)
<223> OTHER INFORMATION: X= Ala or Ile
<220> FEATURE:
<221> NAME/KEY: X
<222> LOCATION: (36)..(36)
<223> OTHER INFORMATION: X= Met or Trp
<220> FEATURE:
<221> NAME/KEY: X
<222> LOCATION: (37)..(37)
<223> OTHER INFORMATION: X= Gly, Thr or Asn
<220> FEATURE:
<221> NAME/KEY: X
<222> LOCATION: (38)..(38)
<223> OTHER INFORMATION: X= Ala, Thr or Leu
<220> FEATURE:
<221> NAME/KEY: X
<222> LOCATION: (39)..(39)
<223> OTHER INFORMATION: X= Ala, Asp or Glu
<220> FEATURE:
<221> NAME/KEY: X
<222> LOCATION: (40)..(40)
<223> OTHER INFORMATION: X= Gln, Asn or Ser
<220> FEATURE:
<221> NAME/KEY: X
<222> LOCATION: (41)..(41)
<223> OTHER INFORMATION: X= Trp or Val
<220> FEATURE:
<221> NAME/KEY: X
<222> LOCATION: (42)..(42)
<223> OTHER INFORMATION: X= Gln or Lys
<220> FEATURE:
<221> NAME/KEY: X
<222> LOCATION: (43)..(43)
<223> OTHER INFORMATION: X= Asn, Thr, Lys or Arg
<220> FEATURE:
<221> NAME/KEY: X
<222> LOCATION: (44)..(44)
<223> OTHER INFORMATION: X= Phe or Val
```

-continued

```
<220> FEATURE:
<221> NAME/KEY: X
<222> LOCATION: (45)..(45)
<223> OTHER INFORMATION: X= His, Ser, Asn
<220> FEATURE:
<221> NAME/KEY: X
<222> LOCATION: (46)..(46)
<223> OTHER INFORMATION: X= Lys, Ala, Thr or Ser
<220> FEATURE:
<221> NAME/KEY: X
<222> LOCATION: (48)..(48)
<223> OTHER INFORMATION: X= Leu, Val or Ile
<220> FEATURE:
<221> NAME/KEY: X
<222> LOCATION: (49)..(49)
<223> OTHER INFORMATION: X= Ile or Val
<220> FEATURE:
<221> NAME/KEY: X
<222> LOCATION: (50)..(50)
<223> OTHER INFORMATION: X= Thr or Lys
<220> FEATURE:
<221> NAME/KEY: X
<222> LOCATION: (51)..(51)
<223> OTHER INFORMATION: X= Ile or Leu
<220> FEATURE:
<221> NAME/KEY: X
<222> LOCATION: (52)..(52)
<223> OTHER INFORMATION: X= Val or Ile
<220> FEATURE:
<221> NAME/KEY: X
<222> LOCATION: (53)..(53)
<223> OTHER INFORMATION: X= Gly or Ser
<220> FEATURE:
<221> NAME/KEY: X
<222> LOCATION: (55)..(55)
<223> OTHER INFORMATION: X= Lys, Ser or Thr
<220> FEATURE:
<221> NAME/KEY: X
<222> LOCATION: (56)..(56)
<223> OTHER INFORMATION: X= Tyr or Phe
<220> FEATURE:
<221> NAME/KEY: X
<222> LOCATION: (57)..(57)
<223> OTHER INFORMATION: X= Val, Leu, Phe or Thr
<220> FEATURE:
<221> NAME/KEY: X
<222> LOCATION: (58)..(58)
<223> OTHER INFORMATION: X= Gln, Ala, Lys or Ser
<220> FEATURE:
<221> NAME/KEY: X
<222> LOCATION: (59)..(59)
<223> OTHER INFORMATION: X59= Gly, Lys, Ser or His
<220> FEATURE:
<221> NAME/KEY: X
<222> LOCATION: (60)..(60)
<223> OTHER INFORMATION: X= Phe, Tyr, Thr or Leu
<220> FEATURE:
<221> NAME/KEY: X
<222> LOCATION: (61)..(61)
<223> OTHER INFORMATION: X= Leu, Thr, Ile, or Val
<220> FEATURE:
<221> NAME/KEY: X
<222> LOCATION: (62)..(62)
<223> OTHER INFORMATION: X=Asp, Asn, Ser or Lys
<220> FEATURE:
<221> NAME/KEY: X
<222> LOCATION: (63)..(63)
<223> OTHER INFORMATION: X= Asn, Asp, Arg or Ala
<220> FEATURE:
<221> NAME/KEY: X
<222> LOCATION: (64)..(64)
<223> OTHER INFORMATION: X= Thr or Val
<220> FEATURE:
<221> NAME/KEY: X
<222> LOCATION: (65)..(65)
<223> OTHER INFORMATION: X= Val, Leu or Ile
<220> FEATURE:
<221> NAME/KEY: X
<222> LOCATION: (66)..(66)
```

<223> OTHER INFORMATION: X= Gly or Ala
<220> FEATURE:
<221> NAME/KEY: X
<222> LOCATION: (67)..(67)
<223> OTHER INFORMATION: X= Ala, Gln, Val or Thr
<220> FEATURE:
<221> NAME/KEY: X
<222> LOCATION: (68)..(68)
<223> OTHER INFORMATION: X= Val, Met, Leu
<220> FEATURE:
<221> NAME/KEY: X
<222> LOCATION: (70)..(70)
<223> OTHER INFORMATION: X= Ser, Asp, Gly

<400> SEQUENCE: 32

Met Met Met Pro Ala Asn Xaa Xaa Xaa Xaa Xaa Xaa Xaa Xaa Xaa
1               5                   10                  15

Xaa Val Xaa Gly Gly Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Asn Xaa
        35                  40                  45

Xaa Xaa Xaa Xaa Xaa Asn Xaa Xaa Xaa Xaa Xaa Xaa Xaa Xaa Xaa
    50                  55                  60

Xaa Xaa Xaa Xaa Phe Xaa Gly
65                  70

<210> SEQ ID NO 33
<211> LENGTH: 10
<212> TYPE: PRT
<213> ORGANISM: Artificial Sequence
<220> FEATURE:
<223> OTHER INFORMATION: consensus sequence
<220> FEATURE:
<221> NAME/KEY: X
<222> LOCATION: (2)..(2)
<223> OTHER INFORMATION: X= Asn, Gly, Ile, Met or Leu
<220> FEATURE:
<221> NAME/KEY: X
<222> LOCATION: (3)..(3)
<223> OTHER INFORMATION: X= Leu or Ala
<220> FEATURE:
<221> NAME/KEY: X
<222> LOCATION: (4)..(4)
<223> OTHER INFORMATION: X= Ala or Ser
<220> FEATURE:
<221> NAME/KEY: X
<222> LOCATION: (5)..(5)
<223> OTHER INFORMATION: X= Ala or Val
<220> FEATURE:
<221> NAME/KEY: X
<222> LOCATION: (6)..(6)
<223> OTHER INFORMATION: X= Ile, Val or Gly
<220> FEATURE:
<221> NAME/KEY: X
<222> LOCATION: (8)..(8)
<223> OTHER INFORMATION: X= Asn or Thr

<400> SEQUENCE: 33

Gly Xaa Xaa Xaa Xaa Xaa Tyr Xaa Leu Gly
1               5                   10

<210> SEQ ID NO 34
<211> LENGTH: 43
<212> TYPE: PRT
<213> ORGANISM: Faecalibacterium prausnitzii

<400> SEQUENCE: 34

Phe Ser Gly Asn Thr Thr Trp Lys Glu Val Gly Asn Ile Gly Lys Asn
1               5                   10                  15

Leu Phe Gly Thr Asn Val Lys Gly Asn Pro Ile Glu Lys Asn Asn Phe
            20                  25                  30

Gly Asp Tyr Ala Met Asn Ala Leu Gly Ile Ala
        35                  40

<210> SEQ ID NO 35
<211> LENGTH: 16
<212> TYPE: PRT
<213> ORGANISM: Faecalibacterium prausnitzii

<400> SEQUENCE: 35

Gly Asn Thr Phe Leu Gln Ser Thr Ile Asn Arg Thr Ile Gly Val Leu
1               5                   10                  15

<210> SEQ ID NO 36
<211> LENGTH: 17
<212> TYPE: PRT
<213> ORGANISM: Faecalibacterium prausnitzii

<400> SEQUENCE: 36

Val Gly Asn Thr Phe Leu Gln Ser Thr Ile Asn Arg Thr Ile Gly Val
1               5                   10                  15

Leu

<210> SEQ ID NO 37
<211> LENGTH: 18
<212> TYPE: PRT
<213> ORGANISM: Faecalibacterium prausnitzii

<400> SEQUENCE: 37

Leu Val Gly Asn Thr Phe Leu Gln Ser Thr Ile Asn Arg Thr Ile Gly
1               5                   10                  15

Val Leu

<210> SEQ ID NO 38
<211> LENGTH: 19
<212> TYPE: PRT
<213> ORGANISM: Faecalibacterium prausnitzii

<400> SEQUENCE: 38

Thr Leu Val Gly Asn Thr Phe Leu Gln Ser Thr Ile Asn Arg Thr Ile
1               5                   10                  15

Gly Val Leu

<210> SEQ ID NO 39
<211> LENGTH: 20
<212> TYPE: PRT
<213> ORGANISM: Faecalibacterium prausnitzii

<400> SEQUENCE: 39

Val Thr Leu Val Gly Asn Thr Phe Leu Gln Ser Thr Ile Asn Arg Thr
1               5                   10                  15

Ile Gly Val Leu
            20

<210> SEQ ID NO 40
<211> LENGTH: 42
<212> TYPE: PRT
<213> ORGANISM: Artificial Sequence
<220> FEATURE:
<223> OTHER INFORMATION: Fragment

<400> SEQUENCE: 40

```
Ile Trp Thr Leu Asp Asn Val Lys Thr Phe Asn Thr Asn Ile Val Thr
1               5                   10                  15

Leu Val Gly Asn Thr Phe Leu Gln Ser Thr Ile Asn Arg Thr Ile Gly
            20                  25                  30

Val Leu Phe Ser Gly Asn Thr Thr Trp Lys
        35                  40

<210> SEQ ID NO 41
<211> LENGTH: 99
<212> TYPE: PRT
<213> ORGANISM: Artificial Sequence
<220> FEATURE:
<223> OTHER INFORMATION: MUT3

<400> SEQUENCE: 41

Met Met Met Pro Ala Asn Tyr Ser Val Ile Ala Glu Asn Glu Met Thr
1               5                   10                  15

Tyr Val Asn Gly Gly Ala Asn Phe Ile Asp Ala Ile Gly Ala Val Thr
            20                  25                  30

Ala Pro Ile Trp Thr Leu Asp Asn Val Lys Thr Phe Asn Thr Asn Ile
        35                  40                  45

Val Thr Leu Val Gly Asn Thr Phe Leu Gln Ser Thr Ile Asn Arg Thr
    50                  55                  60

Ile Gly Val Leu Phe Ser Gly Asn Thr Thr Trp Lys Glu Val Gly Asn
65                  70                  75                  80

Ile Gly Lys Asn Leu Phe Gly Thr Asn Val Lys Gly Asn Pro Ile Glu
                85                  90                  95

Lys Asn Asn

<210> SEQ ID NO 42
<211> LENGTH: 113
<212> TYPE: PRT
<213> ORGANISM: Artificial Sequence
<220> FEATURE:
<223> OTHER INFORMATION: MUT1

<400> SEQUENCE: 42

Asn Phe Ile Asp Ala Ile Gly Ala Val Thr Ala Pro Ile Trp Thr Leu
1               5                   10                  15

Asp Asn Val Lys Thr Phe Asn Thr Asn Ile Val Thr Leu Val Gly Asn
            20                  25                  30

Thr Phe Leu Gln Ser Thr Ile Asn Arg Thr Ile Gly Val Leu Phe Ser
        35                  40                  45

Gly Asn Thr Thr Trp Lys Glu Val Gly Asn Ile Gly Lys Asn Leu Phe
    50                  55                  60

Gly Thr Asn Val Lys Gly Asn Pro Ile Glu Lys Asn Asn Phe Gly Asp
65                  70                  75                  80

Tyr Ala Met Asn Ala Leu Gly Ile Ala Ala Val Tyr Asn Leu Gly
                85                  90                  95

Val Ala Pro Thr Lys Asn Thr Val Lys Glu Thr Glu Val Lys Phe Thr
            100                 105                 110

Val

<210> SEQ ID NO 43
<211> LENGTH: 408
<212> TYPE: DNA
<213> ORGANISM: Faecalibacterium prausnitzii
```

```
<400> SEQUENCE: 43
atgatgatgc ctgcaaacta ctctgttatc gcagagaacg aaatgaccta cgtcaacggt    60
ggcgctaact tcatcgacgc tatcggcgct gttaccgctc ctatctggac tctggacaac   120
gttaagacct tcaacaccaa catcgtgact ctggttggca acaccttcct gcagtccacc   180
attaaccgca ccatcggtgt cctgttcagc ggcaacacca cctggaagga agtcggcaac   240
atcggcaaga acctgttcgg caccaatgtt aagggcaacc cgatcgagaa gaacaacttt   300
ggtgactatg ctatgaacgc tctgggcatt gctgctgctg tctacaacct gggcgtggct   360
cccaccaaga acaccgtcaa ggagactgag gttaagttca ctgtctaa               408

<210> SEQ ID NO 44
<211> LENGTH: 15
<212> TYPE: PRT
<213> ORGANISM: Faecalibacterium prausnitzii

<400> SEQUENCE: 44

Asn Thr Phe Leu Gln Ser Thr Ile Asn Arg Thr Ile Gly Val Leu
1               5                   10                  15

<210> SEQ ID NO 45
<211> LENGTH: 24
<212> TYPE: PRT
<213> ORGANISM: Faecalibacterium prausnitzii

<400> SEQUENCE: 45

Ala Ala Val Tyr Asn Leu Gly Val Ala Pro Thr Lys Asn Thr Val Lys
1               5                   10                  15

Glu Thr Glu Val Lys Phe Thr Val
            20

<210> SEQ ID NO 46
<211> LENGTH: 47
<212> TYPE: PRT
<213> ORGANISM: Faecalibacterium prausnitzii

<400> SEQUENCE: 46

Asn Tyr Ser Val Ile Ala Glu Asn Glu Met Thr Tyr Val Asn Gly Gly
1               5                   10                  15

Ala Asn Phe Ile Asp Ala Ile Gly Ala Val Thr Ala Pro Ile Trp Thr
            20                  25                  30

Leu Asp Asn Val Lys Thr Phe Asn Thr Asn Ile Val Thr Leu Val
        35                  40                  45

<210> SEQ ID NO 47
<211> LENGTH: 17
<212> TYPE: PRT
<213> ORGANISM: Faecalibacterium prausnitzii

<400> SEQUENCE: 47

Lys Gly Asn Thr Phe Leu Gln Ser Thr Ile Asn Arg Thr Ile Gly Val
1               5                   10                  15

Leu

<210> SEQ ID NO 48
<211> LENGTH: 46
<212> TYPE: PRT
<213> ORGANISM: Faecalibacterium prausnitzii

<400> SEQUENCE: 48
```

-continued

```
Val Lys Gly Asn Pro Ile Glu Lys Asn Asn Phe Gly Asp Tyr Ala Met
1               5                   10                  15

Asn Ala Leu Gly Ile Ala Ala Val Tyr Asn Leu Gly Val Ala Pro
            20              25              30

Thr Lys Asn Thr Val Lys Glu Thr Glu Val Lys Phe Thr Val
        35              40              45
```

ANTI-INFLAMMATORY PEPTIDES AND METHODS FOR TREATING INFLAMMATORY DISEASES

The present International patent application claims the priority of the European patent application EP 12008611.1 filed on Dec. 26, 2012, which is herein incorporated by reference.

FIELD OF THE INVENTION

The present invention relates to the treatment of inflammatory diseases based on the discovery of a new anti-inflammatory protein.

BACKGROUND OF THE INVENTION

Inflammation is a natural biological process, which constitutes a normal part of the response to injuries or infections. This process contributes to the protection of the organism against intern or extern aggressions. However, a dysfunction of the inflammation mechanisms, particularly a persistent or too abundant inflammation may cause important painful and life threatening diseases. Such diseases comprise skin disorders, bowel disorders, some neurological disorders, arthritis, autoimmune diseases . . . . Several of these inflammatory diseases remain without treatment or without sufficient treatment. Thus, studying and finding new anti-inflammatory treatment strategies constitutes a major matter in medicine and biomedical research.

Inflammatory bowel disease is a group of disorders characterized by a chronic and relapsing inflammation of the gastrointestinal tract. The most common form of this group is Crohn disease. The pathogenesis involves an inappropriate and ongoing activation of the mucosal immune system driven by the presence of the intestinal microbiota in a genetically predisposed patient.

*Faecalibacterium prausnitzii*, a strictly anaerobic commensal bacterium, has been shown to be decreased in patients with ileal Crohn disease both in faeces and in the mucosal compartment. Its decrease is associated with an early recurrence of the disease in the model of postoperative recurrence after ileo-caecal resection. The culture supernatant of *F. prausnitzii* exerts an anti-inflammatory activity in both in vitro and in vivo murine models of TNBS-induced colitis.

SUMMARY OF THE INVENTION

The present invention is based on the discovery by the present inventors of the anti-inflammatory properties of a protein (and of six derived fragments thereof) of the bacterium *Faecalibacterium prausnitzii*.

The present invention relates to a polypeptide comprising or consisting of the amino acid sequence SEQ ID NO: 1, for use in the treatment or prevention of an inflammatory disease.

Particularly, said inflammatory disease is a bowel inflammatory disease. Preferably, said inflammatory disease is Crohn disease.

The invention further encompasses a nucleic acid sequence encoding a polypeptide of the invention, a vector comprising a nucleic acid of the invention and a host cell comprising a nucleic acid sequence and/or a vector of the invention, for use in the treatment or prevention of an inflammatory disease.

The invention also concerns a pharmaceutical composition comprising a polypeptide, a nucleic acid sequence, a vector or a host cell of the invention and a pharmaceutically acceptable carrier, for the treatment of inflammatory disease.

Finally, the invention provides a method for preventing or treating an inflammatory disease in a patient in need thereof, said method comprising the step of administrating said patient with therapeutically effective amount of a polypeptide, a nucleic acid sequence a vector or a host cell of the invention.

MAM=MAM plasmid transfection comprising protein ZP05614546.1; EMAM=empty MAM plasmid transfection Ecarmal: empty Carma 1 plasmid tranfection.

Figure 2:
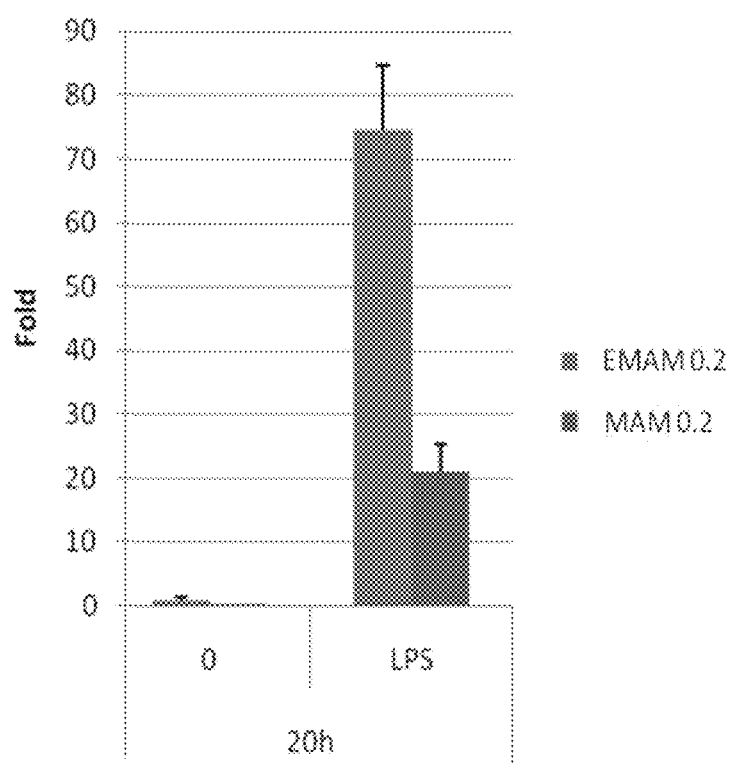

FIG. 2 shows effect of protein ZP05614546.1 (SEQ ID NO: 2) on LPS-dependent NFκB activation using HEK293T cells stably expressing TLR4, MD2 and CD14 and NFκB luciferase reporter.

MAM=MAM plasmid transfection comprising protein ZP05614546.1; EMAM=empty MAM plasmid transfection.

FIG. 3 shows alignments of homolog sequences of the protein of the invention.

*: Amino acid identity, :: Amino acid high homology, .: Amino acid homology.

Figure 4:
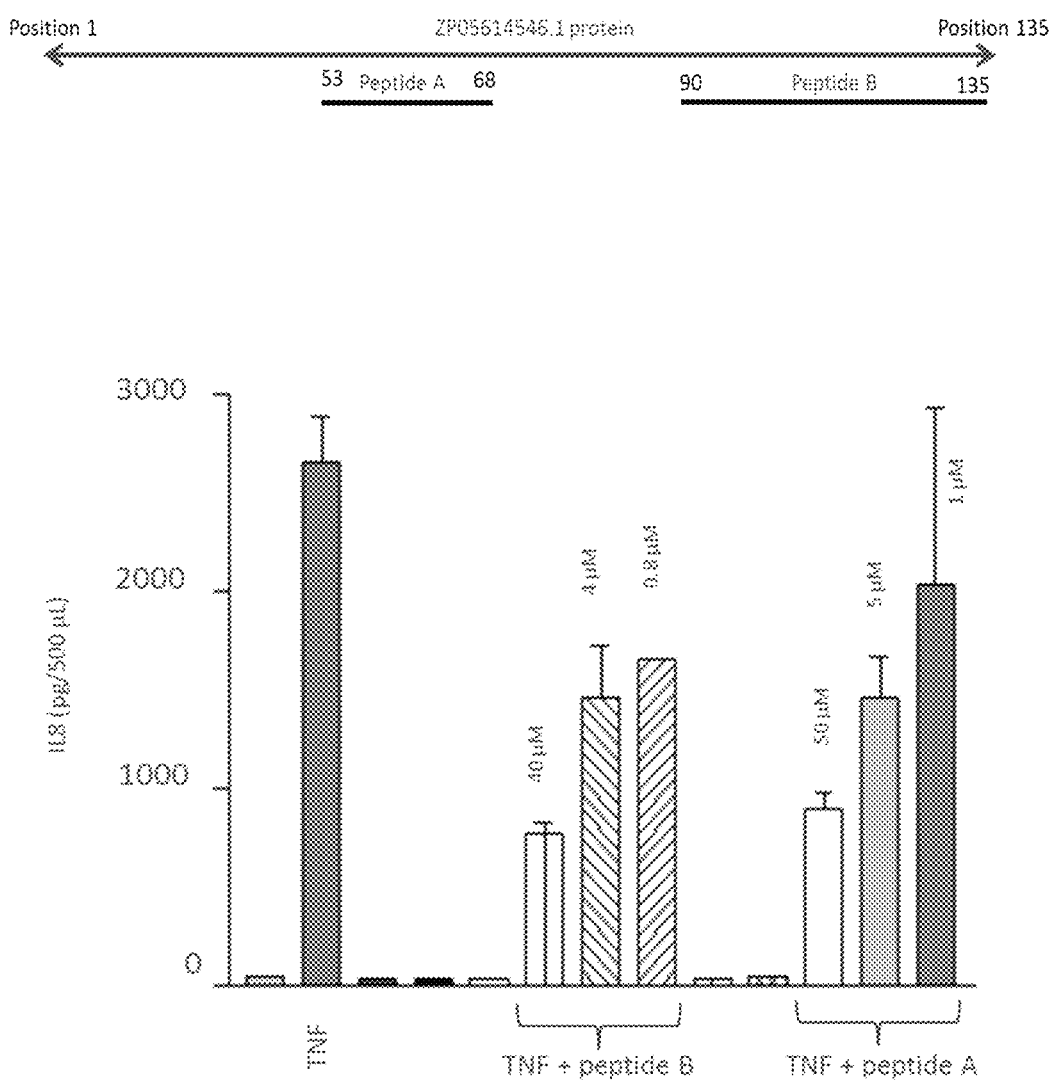

FIG. 4 shows an anti-inflammatory effect of peptides defined by SEQ ID NO: 20-21 on HT29-MTX cells, by an assessment of IL8 production after stimulation of HT29-MTX cells incubated or not with said peptides and stimulated by TNFα.

Figure 5:
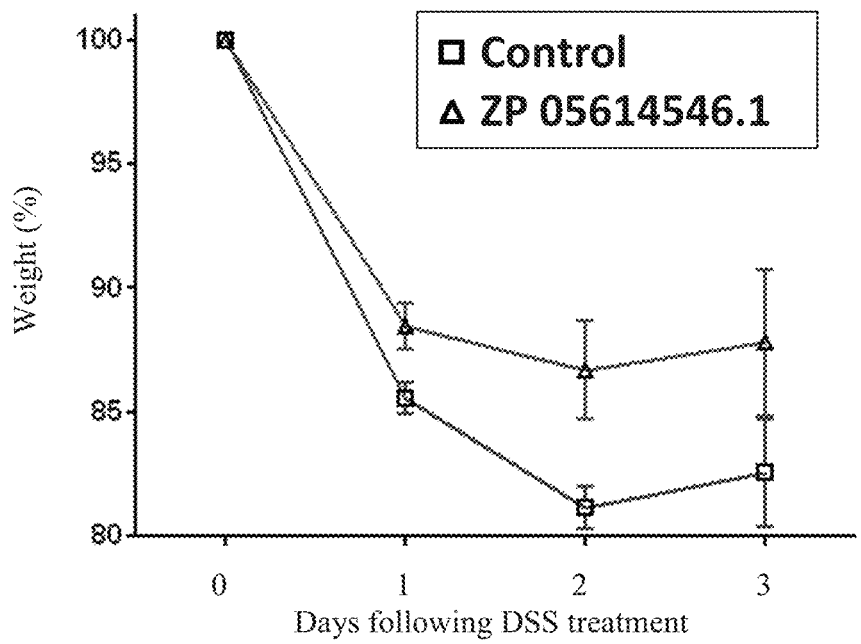

FIG. 5 shows the body weight evolution in the DNBS inflammation model for control mice and ZP 05614546.1 (SEQ ID NO: 2) daily treated mice.

Figure 6:
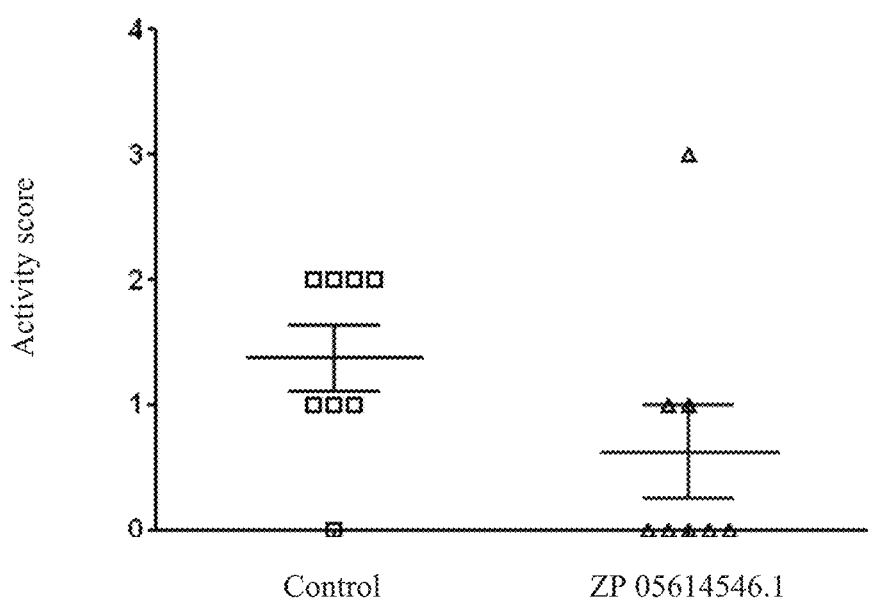

FIG. 6 shows the activity score observed after day 3 following colonic inflammation induction by DNBS for control mice and ZP 05614546.1 (SEQ ID NO: 2) daily treated mice.

Figure 7:
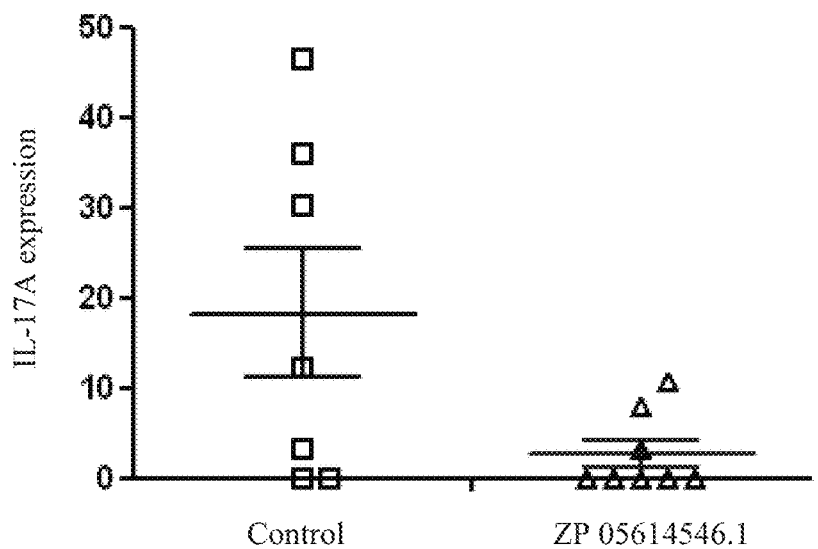

FIG. 7 shows the IL-17A expression for control mice and ZP 05614546.1 (SEQ ID NO: 2) daily treated mice.

Figure 8:
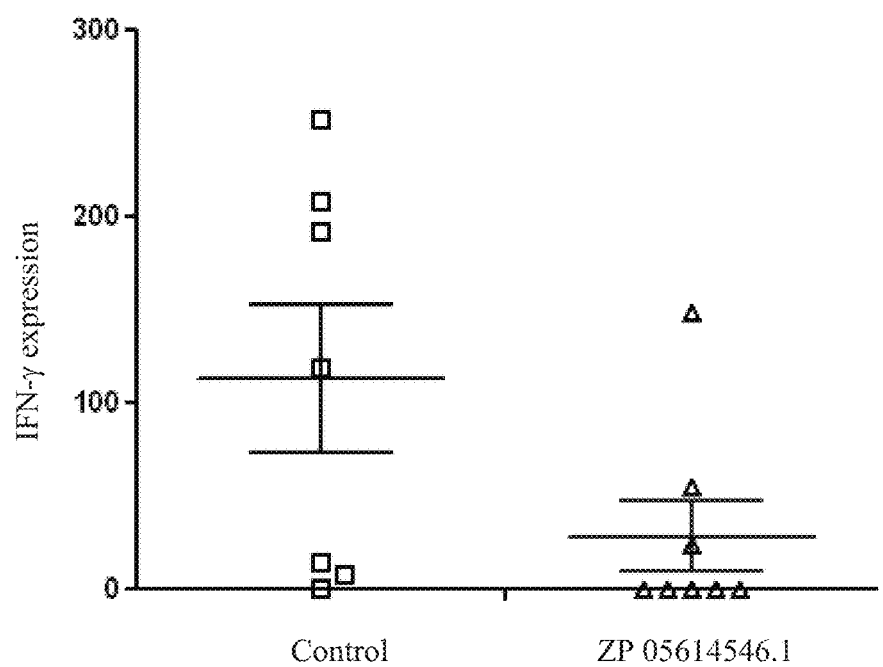

FIG. 8 shows shows the IFN-γ expression for control mice and ZP 05614546.1 (SEQ ID NO: 2) daily treated mice.

Figure 9:
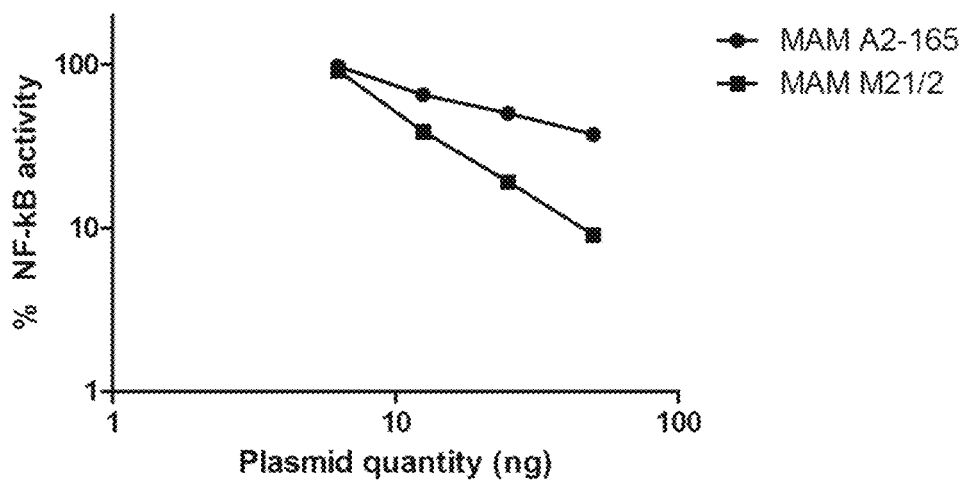

FIG. 9 shows the inhibition of NF-κB activity by ZP 05614546.1 (SEQ ID NO: 2) and SEQ ID NO: 4.

Figure 10:
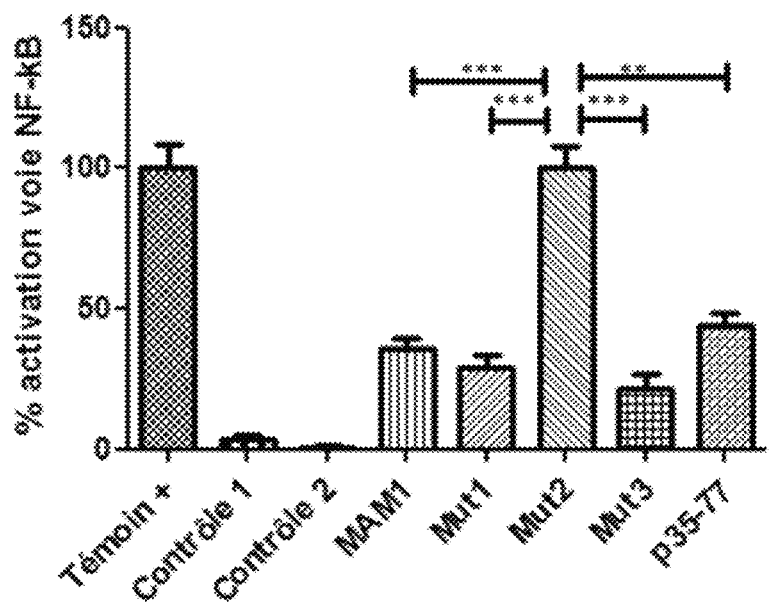

FIG. 10 shows the inhibition of NF-κB activity by ZP 05614546.1 (SEQ ID NO: 2) and mutants thereof.

DETAILED DESCRIPTION OF THE INVENTION

Polypeptides of the Invention

A first aspect of the invention relates to a polypeptide comprising or consisting of the amino acid sequence SEQ ID NO: 1 for use in the treatment or prevention of an inflammatory disease.

The term "inflammatory disease" has its general meaning in the art and refers to any disease and condition associated with inflammation. The term may include, but is not limited to, (1) inflammatory or allergic diseases such as systemic anaphylaxis or hypersensitivity responses, drug allergies, insect sting allergies; inflammatory bowel diseases, such as Crohn disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e. g., atherosclerosis, myositis, inflammatory CNS disorders such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Bechet's syndrome).

In a particular embodiment of the invention, said inflammatory disease is an inflammatory bowel disease, comprising Crohn disease, ulcerative colitis, ileitis and enteritis.

In a preferred embodiment of the invention, said inflammatory disease is Crohn disease.

In the context of the invention, the term "treating" or "treatment" means reversing, alleviating, inhibiting the progress of, or preventing the disorder or condition to which such term applies, or one or more symptoms of such disorder or condition. The term "preventing" or "prevention" refers to preventing the disease or condition from occurring in a subject which has not yet been diagnosed as having it.

In another particular embodiment, said inflammatory disease is an inflammatory disease resulting from an activation of the NFκB pathway.

The polypeptide of the invention comprises or consists of the amino acid sequence SEQ ID NO: 1, or SEQ ID NO: 11. Said sequences correspond to consensus sequence between at least five and nine orthologs protein sequences.

SEQ ID NO: 1

MMMPANX1X2X3X4X5X6X7X8X9X10X11VX12GX13X14X15X16X17X18

X19X20X21X22X23X24X25X26X27X28X29X30X31X32X33X34X35X36X37

X38NX39X40X41X42X43X44NX45X46X47X48X49X50X51X52X53X54X55X

56X57X58FX59GX60X61X62X63X64X65X66X67X68X69X70X71X72X73X74

X75X76X77X78X79X80X81X82X83X84X85X86X87X88X89X90X91X92X93

X94X95X96X97X98X99X100X101X102X103X104X105X106X107X108X109

X110GX111X112X113X114X115YX116LGX117X118X119X120X121X122X123

X124X125X126X127X128X129X130X131X132X133X134X135X136X137X

138X139X140X141X142X143X144X145 X146X147X148X149

Wherein X1 = F, Y; X2 = S, T; X3 = A, V; X4 = V, I; X5 = S, A, N; X6 = E,, —; X7 = N, —;

X8 = E, —; X9 = M, S, A; X10 = T, E; X11 = Y, V; X12 = M, V, N, Y; X13 = G, —,

X14 = S, A; G, —, X15 = N, D, —; X16 = V, F, L, —; X17 = L, I, F, —; X18 = E, D, T, G, —;

X19 = A, I, —; X20 = V, L, I; X21 = A, V, G; X22 = A, D; S, X23 = Y, V, T; X24 = L, T;

X25 = A, P; X26 = P, S; X27 = A, I; V, X28 = M, W; X29 = G, T, N; X30 = A, T, L;

X31 = A, D, E; X32 = Q, N, S; X33 = W, V; X34 = Q, K; X35 = N, T, K, R; X36 = F, V;

X37 = H, S, N; X38 = K, A, T, S; X39 = L, V, I; X40 = I, V; X41 = T, K; X42 = I, L; X43 = V, I;

X44 = G, S; X45 = K, S, T; X46 = Y, F; X47 = V, L, F, T; X48 = Q, A, K, S; X49 = G, K, S, H;

X50 = F, Y, T, L; X51 = L, T, I, V; X52 = D, N, S, K; X53 = N, D, R, A; X54 = T, V;

X55 = V, L, I; X56 = G, A; X57 = A, Q, V, T; X58 = V, M, L; X59 = S, D, G;

X60 = T, N, S, A; X61 = W, Y, T —, X62 = T, V, G, X63 = G, W, P, T, K, S, X64 = G, K, D,

X65 = G, E, D, V; X66 = G, V, PD, X67 = M, D, G, L, K, T, X68 = T, G, S, V, N, I, L,

X69 = G, Y, S, A, I, F,; X70 = F, S, E, G; X71 = G, V, F, A, K, E, D; X72 = G, K, W, N, E;

X73 = Q, N, D, G, L; X74 = F, L, N, Y, F, S, —; X75 = S, D, G, I, —; X76 = K, T, S, N, —;

X77 = I, A, L, D, N, Q, —; X78 = W, Y, S, K, N, T, —; X79 = K, N, G, V, F; —, X80 = K, D, I, F, S, —;

X81 = N, G, V, T, —, X82 = Y, K, I, L, —; X83 = T, G, Y, F, W, —; X84 = D, G, N, —; X85 = N, K, —;

X86 = V, N, —; X87 = T, K, —; X88 = G, D, A, —; X89 = E, L, —; X90 = S, W, —;

X91 = G, F, A, D, V, —; X92 = A, L, V, D, N, G, —, X93 = Q, G, I, D, K, H, R;

X94 = K, N, A, P, G, T, L; X95 = F, W, G, N, T, P; X96 = G, P, R; X97 = Y, F, S, D, I, T, G;

X98 = G, K, D, E, —; X99 = A, E, K, D; X100 = L, V, T, N, M, Q; X101 = G, N, T;

X102 = V, A, G, F; X103 = V, L, F, G; X104 = N, D; X105 = S, A, K, Y;

X106 = I, G, F, A, V, I; X107 = L, M, X108 = N, Q, T; X109 = V, I, G, A, T,; X110 = A, L, V, I;

X111 = N, G, I, M, L; A, X112 = L, G, A; X113 = A, S; X114 = A, V; X115 = I, V, G;

X116 = N, Q, T; X117 = F, S, V, T, M; X118 = G, S, N, A, T, K, X119 = T, S, E, P, D;

X120 = A, I, T; X121 = K, G, A; X122 = N, L, V, K, S, N; X123 = I, E, T, G, L, Y, N;

X124 = V, T, F; X125 = G, K, N, A; X126 = E, S, D, K; X127 = G, V, T, K;

X128 = V, T, K, R, E; X129 = Y, L, F, V, T; X130 = K, P, L, D, G, N;

X131 = A, T, G, V, F, I, S; X132 = L, T, F, N, —; X133 = T, V, G, —; X134 = G, N, K, Q, —;

X135 = K, G, L, V, —; X136 = I, S, W, —; X137 = F, G, —; X138 = D, —; X139 = L, —; X140 = P, —;

X141 = N, —; X142 = N, —; X143 = G, —; X144 = G, —; X145 = S, —; X146 = G, —; X147 = W, —;

X148 = V, —; X149 = G, —; (—: no amino acid).

According to a preferred embodiment, The polypeptide of the invention comprises or consists of the amino acid sequence SEQ ID NO: 11.

SEQ ID NO: 11

MMMPANX1X2X3X4X5X6X7X8X9X10X11VX12GGX13X14X15X16X17X

18X19X20X21X22X23X24X25X26X27X28X29X30X31X32X33X34X35X36X

37NX38X39X40X41X42X43NX44X45X46X47X48X49X50X51X52X53X54X

55X56X57FX58GX59X60X61X62X63X64X65X66X67X68X69X70X71X72X73

X74X75X76X77X78X79X80X81X82X83X84X85X86X87X88X89X90X91X92

X93X94X95X96X97X98X99X100X101X102X103X104X105X106X107X108

X109X110GX111X112X113X114X115YX116LGX117X118X119X120X121X

122X123X124X125X126X127X128X129X130X131X132X133X134X135X136

X137X138X139X140X141X142X143X144X145X146X147X148X149

Wherein X1 = F, Y; X2 = S, T; X3 = A, V; X4 = V, I; X5 = S, A, N; X6 = E, —; X7 = N, —;

X8 = E, —; X9 = M, S, A; X10 = T, E; X11 = Y, V; X12 = M, V, N, Y; X13 = S, A;

X14 = N, D, —; X15 = F, L, —; X16 = I, F, —; X17 = D, T, —; X18 = A, I, —; X19 = V, L, I;

X20 = A, V, G; X21 = A, D; X22 = Y, V, T; X23 = L, T; X24 = A, P; X25 = P, S;

X26 = A, I; X27 = M, W; X28 = G, T, N; X29 = A, T, L; X30 = A, D, E; X31 = Q, N, S;

X32 = W, V; X33 = Q, K; X34 = N, T, K, R; X35 = F, V; X36 = H, S, N; X37 = K, A, T, S;

X38 = L, V, I; X39 = I, V; X40 = T, K; X41 = I, L; X42 = V, I; X43 = G, S; X44 = K, S, T;

X45 = Y, F; X46 = V, L, F, T; X47 = Q, A, K, S; X48 = G, K, S, H; X49 = F, Y, T, L;

X50 = L, T, I, V; X51 = D, N, S, K; X52 = N, D, R, A; X53 = T, V; X54 = V, L, I;

X55 = G, A; X56 = A, Q, V, T; X57 = V, M, L; X58 = S, D, G; X59 = T, N, S; X60 = W, Y, —,

X61 = T, V, G, X62 = P, T, K, S, X63 = G, W, D; X64 = D, K, G; X65 = G, E, D, V, —,

X66 = L, V, K, T; X67 = T, I, G, L; X68 = G, N, F,; X69 = F, Y, I, G; X70 = G, S, E, D;

X71 = G, —; X72 = Q, —; X73 = F, —; X74 = S, V, —; X75 = K, T, —; X76 = I, N, —; X77 = W, L, —; X78 = K, D, E, N; X79 = D, K, N, G; X80 = N, A, L, S, T; X81 = Y, F, I; X82 = T, N, G, S;

X83 = D, T, Q, —; X84 = N, —; X85 = V, —; X86 = T, K, F, —; X87 = G, D; X88 = E, Y, N, L;

X89 = S, G, P, W, Y; X90 = T, I, N; X91 = G, F, E, D, V; X92 = A, G, K, D, N;

X93 = Q, G, N, H, R; X94 = K, N, T, L; X95 = F, W, T, P; X96 = G, R; X97 = Y, F, D, T, G;

X98 = G, Y, D, E, —; X99 = A, D; X100 = L, V, M, Q; X101 = G, N, T; X102 = V, A, F;

X103 = V, L, G; X104 = N, —; X105 = S, A, K, —; X106 = I, G, V, —; X107 = L, M, —;

X108 = N, Q, T, —; X109 = V, I, T, —; X110 = A, L, —; X111 = N, G, I, M, L; X112 = L, A;

X113 = A, S; X114 = A, V; X115 = I, V, G; X116 = N, T; X117 = F, S, V, T, M;

X118 = G, S, A, T, K; X119 = T, S, P, D; X120 = A, I, T; X121 = K, G, A; X122 = N, L, V;

X123 = I, E, T, G, L; X124 = V, T, F; X125 = G, K, N, A; X126 = E, S, D, K; X127 = G, T, K;

X128 = V, T, E, V; X129 = Y, L, V, T; X130 = K, P, G, N; X131 = A, T, FI, S;

X132 = L, T, N, —; X133 = V, G, —; X134 = K, Q, —; X135 = L, V, —; X136 = W, —; X137 = G, —;

X138 = D, —; X139 = L, —; X140 = P, —; X141 = N, —; X142 = N, —; X143 = G, —; X144 = G, —;

X145 = S, —; X146 = G, —; X147 = W, —; X148 = V, —; X149 = G, —; (—: no amino acid).

Advantageously, the polypeptides of the invention is selected in the group comprising SEQ ID NO: 2, SEQ ID NO: 3, SEQ ID NO: 4, SEQ ID NO: 5, SEQ ID NO: 6, SEQ ID NO: 7, SEQ ID NO: 0.8, SEQ ID NO: 9, and SEQ ID NO: 10.

In a particular embodiment, said polypeptide of the invention comprises or consists of the amino acid sequence SEQ ID NO: 2.

Strain A2-165
SEQ ID NO: 2
MMMPANYSVIAENEMTYVNGGANFIDAIGAVTAPIWTLDNVKTFNTNIV

TLVGNTFLQSTINRTIGVLFSGNTTWKEVGNIGKNLFGTNVKGNPIEKNN

FGDYAMNALGIAAAVYNLGVAPTKNTVKETEVKFTV

In another particular embodiment, said polypeptide of the invention comprises or consists of the amino acid sequence SEQ ID NO: 3.

Strain SL3/3
SEQ ID NO: 3
MMMPANFSAVSENEMTYVMGGSVADYLAPAMGAAQWQNFHKNLITIV

GNKYVQGFLDNTVGAVFSGTWTPGDGLTGFGGQFSKIWKDNYTDNVTG

ESTGAQKFGYGALGVVNSILNVAGNLAAIYNLGFGTAKNIVGEGVYKA

In another particular embodiment, said polypeptide of the invention comprises or consists of the amino acid sequence SEQ ID NO: 4.

Strain M21/2
SEQ ID NO: 4
MMMPANFSAVSENEMTYVMGGSVADYLAPAMGAAQWQNFHKNLITIVG

NKYVQGFLDNTVGAMFSGTWTPGDGLTGFGGQFSTIWKKNYTDNVTDES

TGAQKFGYGALGVVNSILNVAGNLAAIYNLGFGTAKNIVGEGVYKA

In another particular embodiment, said polypeptide of the invention comprises or consists of the amino acid sequence SEQ ID NO: 5.

Strain KLE1255
SEQ ID NO: 5
MMMPANFSAVAENEMTYVVGGSLVDVLAPAMTTANWQNVSANVIKIVG

NSFLAKYTNDVLAQLFDGNYVPGDVIGYSVKNLDKAYNKGYGTFGGNW

GFAVGALNAGMQILGGLSAIYTLGSSSIGLETKSGTLPTL

In another particular embodiment, said polypeptide of the invention comprises or consists of the amino acid sequence SEQ ID NO: 6.

Strain L2-61
SEQ ID NO: 6
MMMPANFTAVNSEVVYGGADLFTILADTTAPIWNAANVKKFNTNLITLIS

NSFFKKTVSNTLGVMFGGNWGKDGDKIFGEEGSINQNVFGLWNDDHTTR

TDDMTFGNKVMQVLGMAAVGYTLGTTDAKVGFNDGVYGINGKL

In another particular embodiment, said polypeptide of the invention comprises or consists of the amino acid sequence SEQ ID NO: 7.

Strain L2-62
SEQ ID NO: 7
MMMPANFSAVNAEVVYGGAVADYLPSAWTAESVKRFNSNIITLVSNS

FTSHLLKATLGTMFSGSWGSDGVTLFGDNGTFSGLYNVNRLPGGEAQT

FGNKIMTTLGLASVVYTLGMKDAAVLTAKKVTNSNGQVWGDLPNNG

GSGWVG

In another particular embodiment, said polypeptide of the invention comprises or consists of the amino acid sequence SEQ ID NO: 8.

Strain CAG: 821
SEQ ID NO: 8
MMMPANFSVVAENEMTYVVGGGVIEAIGSVTAPIWTTANVKTFNTNLV

TIIGNSYVSKLVGATLGVMFGGNWGGDGPMSSFFGDNGSLSGIVKYGIA

GGSKELNGFNKFMQVVGLGAAVYQLGTNETKKYVKEVKFLGTTGKI

In another particular embodiment, said polypeptide of the invention comprises or consists of the amino acid sequence SEQ ID NO: 9.

Strain CAG: 822
SEQ ID NO: 9
MMMPANYSAIAENEMTYVVGGGLLEAIGSVTAPVWGAANVKTFNTNLI

TIIGNSYVSKVLGATLGVMFSGAWGTKDDDVAEAWGYDKDKKITIFGK

NKALWNALDPNGDKETNGFNKFMQGIGALAAVYTLGTSTTKSNVAEG

RYDVFGNGSF

In another particular embodiment, said polypeptide of the invention comprises or consists of the amino acid sequence SEQ ID NO: 10

Strain CNCM-4573
SEQ ID NO: 10
MMMPANFSAVSENEMTYVMGGSIADYLAPAMGAAQWQNFHKNLVTI

VGNKYVQGFLDNTVGAVFSGTWTPGVGLTGFGGQFSTIWKKNYTDNV

TDESTGAQKFGYGALGVVNSILNVAGNLAAIYNLGFGTAKNIVGEGVY

KA

More preferably, the polypeptides of the invention is selected in the group consisting of SEQ ID NO: 2, SEQ ID NO: 3, SEQ ID NO: 4, SEQ ID NO: 5, SEQ ID NO: 7, and SEQ ID NO: 10

As used herein, the polypeptide of the invention encompasses derivatives or fragments thereof.

According to the invention, the term "derivative thereof" has its general meaning in the art and corresponds to an amino acid sequence or a nucleic acid sequence having at least 90% sequence identity to the referred amino acid sequence or nucleic acid sequence respectively, particularly 95%, and preferably 99%. The term "percentage of identity between two amino acid sequences" or "percentage of identity between two nucleic sequences" refers to the percentage of identic nucleotides or amino acids between two compared sequences, said percentage being obtained with the best alignment of the whole sequence. The term "best alignment" means the alignment that permits to obtain the most elevated identity percentage. It can be realized by using various algorithms and methods well known in the art and computer programs based on said algorithms (GAP, BESTFIT, BLAST P, BLAST N, FASTA, TFASTA, Genetics Computer Group, 575 Science Dr., Madison, Wis. USA). Preferably, the BLAST algorithm is used.

According to the invention, the term "fragment" refers to a polypeptide being a part of an amino acid sequence of interest and having a length of at least 10 amino acids, particularly at least 15 amino acids, more particularly at least 20 amino acids, preferably at least 30 amino acids, more preferably at least 40 amino acids. Preferably, said fragment has a length of less than 120 amino acids, particularly less than 110 amino acids, preferably less than 100 amino acids, and more preferably less than 50 amino acids. The term is transposable to fragments of nucleic acid sequences.

According to the invention, said derivative and/or fragment of a polypeptide of the invention are conservative derivative or conservative fragments thereof.

By "conservative fragments" and "conservative derivatives" of a polypeptide of the invention, it is respectively meant fragments and derivatives which retain the function, namely the anti-inflammatory properties, of said a polypeptide of the invention. More specifically, a fragment or a derivative inhibiting the secretion of IL-8 by HT29-MTX cells from at least 50% at a concentration of 100 μM or less. Such conservative fragments and conservative derivatives are functional equivalents of said polypeptide. They are "conservative" because they retain the biological function of the original polypeptide, more particularly because they retain an equivalent anti-inflammatory effect.

The inventors have established that the MAM anti-inflammatory properties are carried out by the p49-70 portion of SEQ ID NO: 2 (VTLVGNTFLQSTINRTIGVL; SEQ ID NO: 12) and reproducibly by the p35-77 portion of SEQ ID NO: 2 (IWTLDNVKTFNTNIVTLVGNTFLQSTINRTIGVLFSGNTTWKE; SEQ ID NO: 13).

Accordingly, said conservative fragment of the invention comprises or consists of the amino acid sequence SEQ ID NO: 14 and derivatives thereof. Said sequence corresponds to consensus sequence between nine MAM orthologs of SEQ ID NO: 12.

SEQ ID NO: 14
X1X2X3X4X5NX6X7X8X9X10X11X12X13X14X15X16X17X18X19

Wherein X1 = I, V; X2 = T, K; X3 = I, L; X4 = V, I; X5 = G, S; X6 = K, S, T; X7 = Y, F; X8 = V, L, F, T; X9 = Q, A, K, S; X10 = G, K, S, H; X11 = F, Y, T, L; X12 = L, T, I, V; X13 = D, N, S, K; X14 = N, D, R, A; X15 = T, V; X16 = V, L, I; X17 = G, A; X18 = A, Q, V, T; X19 = V, M, L Preferably, said conservative fragment comprises or consists of a polypeptide selected in the group comprising:

| | |
|---|---|
| VTLVGNTFLQSTINRTIGVL | SEQ ID NO: 12 |
| ITIVGNKYVQGFLDNTVGAV | SEQ ID NO: 15 |
| ITIVGNKYVQGFLDNTVGAM | SEQ ID NO: 16 |
| IVGNSFLAKYTNDVLAQL | SEQ ID NO: 17 |
| ITLISNSFFKKTVSNTLGVM | SEQ ID NO: 18 |
| ITLVSNSFTSHLLKATLGTM | SEQ ID NO: 19 |
| VTIIGNSYVSKLVGATLGVM | SEQ ID NO: 20 |
| ITIIGNSYVSKVLGATLGVM | SEQ ID NO: 21 |
| IVGNKYVQGFLDNTVGAV | SEQ ID NO: 22 | and derivatives thereof.

In another embodiment, said conservative fragment of the invention comprises or consists of the amino acid sequence SEQ ID NO: 23 and derivatives thereof. Said sequence corresponds to a consensus sequence between nine MAM orthologs of SEQ ID NO: 13 and derivatives thereof.

SEQ ID NO: 23
X1X2X3X4X5X6X7X8X9X10X11X12NX13X14X15X16X17X18NX19 X20X21X22X23X24X25X26X27X28X29X30X31X32FX33GX34X35 X36X37X38X39

Wherein X1 = A, I; V, X2 = M, W; X3 = G, T, N; X4 = A, T, L; X5 = A, D, E; X6 = Q, N, S; X7 = W, V; X8 = Q, K; X9 = N, T, K, R; X10 = F, V; X11 = H, S, N; X12 = K, A, T, S; X13 = L, V, I; X14 = I, V; X15 = T, K; X16 = I, L; X17 = V, I; X18 = G, S; X19 = K, S, T; X20 = Y, F; X21 = V, L, F, T; X22 = Q, A, K, S; X23 = G, K, S, H; X24 = F, Y, T, L; X25 = L, T, I, V; X26 = D, N, S, K; X27 = N, D, R, A; X29 = T, V; X30 = V, L, I; X31 = G, A; X32 = A, Q, V, T; X32 = V, M, L X34 = S, D, G; X35 = T, N, S, A; X36 = W, Y, T −, X36 = T, V, G, X37 = G, W, P, T, K, S, X39 = G, K, D, X40 = G, E, D, V (−: no amino acids)

Preferably, said conservative fragment comprises or consists of a polypeptide selected in the group comprising:

SEQ ID NO: 13
IWTLDNVKTFNTNIVTLVGNTFLQSTINRTIGVLFSGNTTWKE

SEQ ID NO: 24
AMGAAQWQNFHKNLITIVGNKYVQGFLDNTVGAVFSGTWTPGD

SEQ ID NO: 25
AMGAAQWQNFHKNLITIVGNKYVQGFLDNTVGAMFSGTWTPGD

SEQ ID NO: 26
AMTTANWQNVSANVIKIVGNSFLAKYTNDVLAQLFDGNYVPGD

SEQ ID NO: 27
IWNAANVKKF NTNLITLISN SFFKKTVSNT LGVMFGGNWG KDG

SEQ ID NO: 28
AWTAESVKRFNSNIITLVSNSFTSHLLKATLGTMFSGSWGSDG

SEQ ID NO: 29
IWTTANVKTFNTNLVTIIGNSYVSKLVGATLGVMFGGNWGGDG

SEQ ID NO: 30
VWGAANVKTFNTNLITIIGNSYVSKVLGATLGVMFSGAWGTKD

SEQ ID NO: 31
AMGAAQWQNFHKNLVTIVGNKYVQGFLDNTVGAVFSGTWTPGV and derivatives thereof.

In another particular embodiment, said conservative fragment of the invention comprises or consists of a polypeptide chosen among SEQ ID NO: 32-42 and derivatives thereof.

SEQ ID NO: 32
MMMPANX1X2 X3X4X5X6X7X8X9X10 X11VX12GGX13X14X15 X16X17X18X19X20 X21X22X23X24X25 X26X27X28X29X30 X31X32X33X34X35 X36X37NX38X39X40 X41X42X43NX44X45 X46X47X48X49X50 X51X52X53X54X55 X56X57FX58G

Wherein X1 = F, Y; X2 = S, T; X3 = A, V; X4 = V, I; X5 = S, A, N; X6 = E, −; X7 = N, −; X8 =E, −; X9 = M, S, A; X10 = T, E; X11 = Y, V; X12 = M, V, N, Y; X13 = S, A; X14 = N, D, −; X15 = F, L, −; X16 = I, F, −; X17 = D, T, −; X18 = A, I, −; X19 = V, L, I; X20 = A, V, G; X21 = A, D; X22 = Y, V, T; X23 = L, T; X24 = A, P; X25 = P, S; X26 = A, I; X27 = M, W; X28 = G, T, N; X29 = A, T, L; X30 = A, D, E; X31 = Q, N, S; X32 = W, V; X33 = Q, K; X34 = N, T, K, R; X35 = F, V; X36 = H, S, N; X37 = K, A, T, S; X38 = L, V, I; X39 = I, V; X40 = T, K; X41 = I, L; X42 = V, I; X43 = G, S; X44 = K, S, T; X45 = Y, F; X46 = V, L, F, T; X47 = Q, A, K, S; X48 = G, K, S, H; X49 = F, Y, T, L; X50 = L, T, I, V; X51 = D, N, S, K; X52 = N, D, R, A; X53 = T, V; X54 = V, L, I; X55 = G, A; X56 = A, Q, V, T; X57 = V, M, L; X58 = S, D, G;

SEQ ID NO: 33
GX111X112X113 X114X115 YX116LG

Wherein X111 = N, G, I, M, L; X112 = L, A; X113 = A, S; X114 = A, V; X115 = I, V, G; X116 = N, T

SEQ ID NO: 34
FSGNTTWKEVGNIGKNLFGTNVKGNPIEKNNFGDYAMNALGIA

SEQ ID NO: 35
GNTFLQSTINRTIGVL

SEQ ID NO: 36
VGNTFLQSTINRTIGVL

SEQ ID NO: 37
LVGNTFLQSTINRTIGVL

SEQ ID NO: 38
TLVGNTFLQSTINRTIGVL

SEQ ID NO: 39
VTLVGNTFLQSTINRTIGVL

SEQ ID NO: 40
IWTLDNVKTFNTNIVTLVGNTFLQSTINRTIGVLFSGNTTWK

Mut3

SEQ ID NO: 41
MMMPANYSVIAENEMTYVNGGANFIDAIGAVTAPIWTLDNVKTFNTNIV TLVGNTFLQSTINRTIGVLFSGNTTWKEVGNIGKNLFGTNVKGNPIEKNN

Mut 1

SEQ ID NO: 42
NFIDAIGAVTAPIWTLDNVKTFNTNIVTLVGNTFLQSTINRTIGVLFSGN TTWKEVGNIGKNLFGTNVKGNPIEKNNFGDYAMNALGIAAAVYNLGVAPT KNTVKETEVKFTV

In another particular embodiment, the polypeptide of the invention corresponds to an amino acid sequence having in the N-term to C-term orientation:
the sequence SEQ ID NO: 32; and
the sequence SEQ ID NO: 33, wherein the sequence SEQ ID NO: 32 and SEQ ID NO: 33 are preferably spaced from 80 to 10 amino acids, preferably from 60 to 15 amino acids, and more preferably from 40 to 20 amino acids.

In a preferred embodiment, a polypeptide of the invention or a derivative or a fragment thereof is isolated.

As used herein, the term polypeptide encompasses polypeptides or proteins following post-translational modifications such as glycosylation, phosphorylation or other modifications of some amino acid residues.

The present invention thus relates to a polypeptide as described for use as an anti-inflammatory drug.

As used herein, the term "anti-inflammatory drug" refers to a drug that directly or indirectly reduces inflammation in a tissue.

A polypeptide of the invention may be produced by conventional automated peptide synthesis methods or by recombinant expression. General principles for designing and making peptides and proteins are well known to those of skill in the art.

A polypeptide of the invention may be synthesized in solution or on a solid support in accordance with conventional techniques. Various automatic synthesizers are commercially available and can be used in accordance with known protocols. A polypeptide of the invention may also be synthesized by solid-phase technology employing an exemplary peptide synthesizer such as a MODEL 433A from APPLIED BIOSYSTEMS INC. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems, including mammalian cell systems. Those of skill in the art are aware of various techniques for optimizing mammalian expression of proteins. Mammalian cells that are useful in recombinant protein productions include, but are not limited to, VERO cells, HeLa cells, Chinese hamster ovary (CHO) cell lines, COS cells (such as COS-7), W138, BHK, HepG2, Caco-2, HT29, HEK, HCT 116, 3T3, RIN, MDCK, A549, PC12, K562 and 293 cells.

Exemplary protocols for the recombinant expression of the peptide substrates or fusion polypeptides in bacteria, yeast and other invertebrates are known to those of skill in the art and a briefly described herein below.

In the recombinant production of the polypeptide of the invention, it would be necessary to employ vectors comprising a nucleic acid sequence encoding such a polypeptide.

Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation.

The choice of a suitable expression vector for expression of the polypeptide of the invention will of course depend upon the specific host cell to be used, and is within the skill of the ordinary artisan.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the nucleic acid sequence encoding the polypeptide of interest (i.e., a polypeptide of the invention, a derivative or fragment thereof and the like). Thus, a promoter nucleotide sequence is operably linked to a given DNA sequence if the promoter nucleotide sequence directs the transcription of the sequence.

Similarly, the phrase "under transcriptional control" means that the promoter is in the correct location and orientation in relation to the nucleic acid to control RNA polymerase initiation and expression of the gene. Any promoter that will drive the expression of the nucleic acid may be used. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Common promoters include, e.g., the human cytomegalovirus (CMV) immediate early gene promoter, the SV40 early promoter, the Rous sarcoma virus long terminal repeat, [beta]-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient to produce a recoverable yield of protein of interest. By employing a promoter with well known properties, the level and pattern of expression of the protein of interest following transfection or transformation can be optimized. Inducible promoters also may be used.

Another regulatory element that is used in protein expression is an enhancer. These are genetic elements that increase transcription from a promoter located at a distant position on the same molecule of nucleic acid. Where an expression construct employs a cDNA insert, one will typically desire to include a polyadenylation signal sequence to effect proper polyadenylation of the gene transcript. Any polyadenylation signal sequence recognized by cells of the selected transgenic animal species is suitable for the practice of the invention, such as human or bovine growth hormone and SV40 polyadenylation signals.

The protein identified by the inventors seems to comprise glycosylation sites. So, the host systems preferably used are able to glycosylate the polypeptide of the invention. Those skilled in the art are able to choose such systems. Examples of host cells that can be used comprise, but are not limited to, *Lactobacillus plantarum* cells or *Lactobacillus rhamnosus*.

Nucleic Acids, Vectors and Host Cells of the Invention

A second object of the invention relates to a nucleic acid sequence encoding a polypeptide of the invention for use in the treatment or prevention of an inflammatory disease.

In a particular embodiment of the invention, said inflammatory disease is an inflammatory bowel disease.

In a preferred embodiment of the invention, said inflammatory disease is Crohn disease.

In another particular embodiment, said inflammatory disease is an inflammatory disease resulting from an activation of the NFκB pathway.

As used herein, said nucleic acid sequence may be a DNA or a RNA sequence.

In a particular embodiment of the invention, said nucleic acid sequence encodes a polypeptide comprising or consisting of the nucleic acid sequence SEQ ID NO: 2-7 and SEQ ID NO: 8-18.

In a preferred embodiment, said nucleic acid sequence encodes a polypeptide comprising or consisting of the nucleic acid sequence SEQ ID NO: 2.

In a more preferred embodiment of the invention, said nucleic acid sequence encoding a polypeptide of the invention comprises or consists of the nucleic acid sequence defined by SEQ ID NO: 43.

```
                                              SEQ ID NO: 43
ATG ATG ATG CCT GCA AAC TAC TCT GTT ATC GCA GAG

AAC GAA ATG ACC TAC GTC AAC GGT GGC GCT AAC TTC

ATC GAC GCT ATC GGC GCT GTT ACC GCT CCT ATC TGG

ACT CTG GAC AAC GTT AAG ACC TTC AAC ACC AAC ATC

GTG ACT CTG GTT GGC AAC ACC TTC CTG CAG TCC ACC

ATT AAC CGC ACC ATC GGT GTC CTG TTC AGC GGC AAC

ACC ACC TGG AAG GAA GTC GGC AAC ATC GGC AAG AAC

CTG TTC GGC ACC AAT GTT AAG GGC AAC CCG ATC GAG

AAG AAC AAC TTT GGT GAC TAT GCT ATG AAC GCT CTG

GGC ATT GCT GCT GCT GTC TAC AAC CTG GGC GTG GCT

CCC ACC AAG AAC ACC GTC AAG GAG ACT GAG GTT AAG

TTC ACT GTC TAA
```

As used herein, said nucleic acid sequence encompasses derivatives or fragments thereof. Preferably, said derivatives or fragments are conservative derivatives or fragments.

In a preferred embodiment, said nucleic acid sequence, derivative or fragment thereof is isolated.

A third object of the invention relates to a vector comprising a nucleic acid sequence of the invention for use in the treatment or prevention of an inflammatory disease.

In a particular embodiment of the invention, said inflammatory disease is an inflammatory bowel disease.

In a preferred embodiment of the invention, said inflammatory disease is Crohn disease.

In another particular embodiment, said inflammatory disease is an inflammatory disease resulting from an activation of the NFκB pathway.

The term "vector" (or "cloning vector" and "expression vector") means the vehicle by which a nucleic acid sequence can be introduced into a host cell, so as to transform the host and promote expression (e.g. transcription and translation) of the introduced sequence.

Typically, a nucleic acid sequence of the invention may be included in any suitable vector, such as a plasmid, cosmid, episome, artificial chromosome, phage or a viral vector.

Such vectors may comprise regulatory elements, such as a promoter, enhancer, terminator and the like, to cause or direct expression of said polypeptide upon administration to a subject. Examples of promoters and enhancers used in the expression vector for animal cell are well known in the art and include early promoter and enhancer of SV40, LTR promoter and enhancer of Moloney mouse leukemia virus, promoter and enhancer of immunoglobulin H chain and the like.

According to the invention, any expression vector for animal cell can be used, so long as a nucleic acid sequence of the invention can be inserted and expressed. Examples of suitable vectors include pAGE107, pAGE103, pHSG274, pKCR, pSG1 beta d2-4 and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO94/19478.

A fourth object of the present invention relates to a host cell which has been transfected, infected or transformed by a nucleic acid sequence and/or a vector of the invention for use in the treatment or prevention of an inflammatory disease.

In a particular embodiment of the invention, said inflammatory disease is an inflammatory bowel disease.

In a preferred embodiment of the invention, said inflammatory disease is Crohn disease.

In another particular embodiment, said inflammatory disease is an inflammatory disease resulting from an activation of the NFκB pathway.

The term "transformation" means the introduction of a "foreign" nucleic acid sequence to a host cell, so that the host cell will express the introduced sequence to produce a desired substance, typically a polypeptide encoded by the introduced sequence. A host cell that receives and expresses introduced DNA or RNA has been "transformed".

Examples of host cells that may be used for the invention are well known in the art, and some of them are described above.

The protein identified by the inventors seems to comprise glycosylation sites. So, the host cells used are preferably able to glycosylate the polypeptide of the invention. Those skilled in the art are able to choose such systems. Examples of host cells that can be used comprise, but are not limited to, *Lactobacillus plantarum* cells or *Lactobacillus rhamnosus*.

In a particular embodiment of the invention, said host cell may be a probiotic.

Said probiotic is a is a host cell, generally a bacterium or yeast cell, which has been transfected, infected or transformed by a nucleic acid sequence and/or a vector of the invention.

Examples of host cells that can be used comprise, but are not limited to, *Bacillus coagulans, Bifidobacterium animalis, Bifidobacterium longum, Lactobacillus acidophilus, Lactobacillus paracasei, Lactobacillus johnsonii, Lactobacillus plantarum, Lactobacillus reuteri, Lactobacillus reuteri Protectis, Saccharomyces boulardii, Lactobacillus rhamnosus, Lactobacillus acidophilus, Lactobacillus acidophilus, Lactobacillus bulgaricus, Streptococcus thermophiles, Lactobacillus bifidus*.

Vectors and host cells of the invention are adapted to an administration in patients, preferably humans. One skilled in the art can easily choose such vectors and host cells.

In one embodiment, the invention relates to a nucleic acid, vector or host cell of the invention for use as an anti-inflammatory drug.

According to the invention, the nucleic acid sequence, vector and host cell of the invention may be used to produce a recombinant polypeptide of the invention in a suitable expression system.

Pharmaceutical Compositions and Therapeutic Methods of the Invention

A fifth object of the invention relates to a pharmaceutical compositions comprising a polypeptide of the invention, a nucleic acid sequence of the invention, a vector of the invention or a host cell of the invention and a pharmaceutically acceptable carrier.

In one embodiment, the invention relates to said pharmaceutical composition for the treatment of inflammatory disease.

In a more particular embodiment of the invention, said inflammatory disease is an inflammatory bowel disease.

In a preferred embodiment of the invention, said inflammatory disease is Crohn disease.

In another particular embodiment, said inflammatory disease is an inflammatory disease resulting from an activation of the NFκB pathway.

The term "pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The polypeptide, nucleic acid sequence, vector or host cell of the invention may be combined with pharmaceutically acceptable excipients, and optionally sustained-release matrices, such as biodegradable polymers, to form therapeutic compositions.

In general, polypeptide, nucleic acid sequence, vector or host cell of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral, using a convenient daily dosage regimen which can be adjusted according to the degree of affliction.

A polypeptide, nucleic acid sequence, vector or host cell of the present invention, together with one or more conventional adjuvants, carriers, or diluents, may be placed into the form of pharmaceutical compositions and unit dosages. The pharmaceutical compositions and unit dosage forms may comprise conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The polypeptide, nucleic acid sequence, vector or host cell of the present invention may be formulated in a wide variety of oral administration dosage forms. The pharmaceutical compositions and dosage forms may comprise a polypeptide, nucleic acid sequence, vector or host cell of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, gum tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents.

Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The polypeptide, nucleic acid sequence, vector or host cell of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents.

Alternatively, the active ingredient may be in powder form, obtained by aseptic isolation of sterile solid or by lyophilization from solution for constitution before use with a suitable vehicle, e.g., sterile, pyrogen-free water.

The polypeptide, nucleic acid sequence, vector or host cell of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or gum tragacanth; pastilles comprising the active ingredient in an inert base such as gelatin and glycerin or sucrose and acacia; and mouthwashes comprising the active ingredient in a suitable liquid carrier.

The polypeptide, nucleic acid sequence, vector or host cell of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The polypeptide, nucleic acid sequence, vector or host cell of the present invention may be formulated for vaginal administration.

Pessaries, tampons, creams, gels, pastes, foams or sprays containing in addition to the active ingredient such carriers as are known in the art to be appropriate.

The polypeptide, nucleic acid sequence, vector or host cell of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The polypeptide, nucleic acid sequence, vector or host cell of the present invention may be formulated for aerosol administration, particularly to the respiratory tract and including intranasal administration. The compound will generally have a small particle size for example of the order of five (5) microns or less.

Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, nitrogen, nitrous oxide, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support.

Other pharmaceutically acceptable forms include, e.g. tablets or other solids for oral administration; time release capsules; and any other form currently used. Non degradable capsules, or gastro-resistant capsules may also be used. Such pharmaceutical forms are well known in the art.

In certain embodiments, the use of liposomes and/or nanoparticles is contemplated for the administration of polypeptide, nucleic acid sequence, vector or host cell of the present invention. Liposomes are particularly suitable for an oral administration of a hydrophobic compound. The formation and use of liposomes and/or nanoparticles are known to those of skill in the art.

In the particular embodiment of the treatment of an inflammatory bowel disease, more particularly Crohn disease, an oral or a rectal administration are preferred. For oral administration, gastro-resistant, non degradable and time release capsules are preferred.

In the particular embodiment of a composition of the invention comprising a host cell of the invention which is a probiotic, the composition may be used by oral administration.

In general, the polypeptide, nucleic acid sequence, vector or host cell of the present invention will be administered in a therapeutically effective amount by any of the accepted modes of administration for agents that serve similar utilities. Suitable dosage ranges are typically about 1-500 mg daily, preferably about 1-100 mg daily, and most preferably about 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

A sixth object of the invention relates to a method for preventing or treating an inflammatory disease in a patient in need thereof, said method comprising the step of administrating said patient with therapeutically effective amount of a polypeptide, a nucleic acid sequence a vector or a host cell of the invention.

In a particular embodiment of the invention, said inflammatory disease is an inflammatory bowel disease.

In a preferred embodiment of the invention, said inflammatory disease is Crohn disease.

The term "patient" refers to any subject, preferably a human, afflicted with or susceptible to be afflicted with an inflammatory disease.

The terms "effective amount" and "therapeutically effective amount" refer to a sufficient amount of the agent to provide the desired biological result at a reasonable benefit/risk ratio applicable to any medical treatment. That result can be prevention, reduction and/or alleviation of the signs, symptoms, or causes of a disease, or any other desired alteration of a biological system having or at risk of having such signs, symptoms, or disease. An appropriate "effective" amount in any individual case may be determined by one of ordinary skill in the art using routine experimentation.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

EXAMPLES

The following examples describe some of the preferred modes of making and practicing the present invention. However, it should be understood that the examples are for illustrative purposes only and are not meant to limit the scope of the invention.

Example 1. Identification of the Molecule(s) Responsible for the Anti-Inflammatory Effect of *Faecalibacterium prausnitzii*

1. Identification of Six Peptides Only Present in the Supernatant of *F. prausnitzii*.

Further to the knowledge of SOKOL et al., PNAS, 2008, the present inventors first tried to identify the molecules responsible for the anti-inflammatory effect of *Faecalibacterium prausnitzii*. Nevertheless, this determination was clearly unpredictable because of the difficulty to cultivate *F. prausnitzii*, which microorganism is strictly anaerobic. Moreover, the characterization of this microorganism being very recent, its characteristics, specificities, taxonomy, etc. are essentially unknown further complicating its use as an experimental model.

1.1. Culture of *F. prausnitzii*

The culture of the *F. prausnitzii* was difficult, in part due to the sensitivity of the bacterium and to the necessity of anaerobia conditions.

1.2. Fractionation of the *F. prausnitzii* Culture Medium

A solid/liquid extraction of 3 ml of medium on Waters Oasis HLB® SPE cartridges was carried out to fractionated culture supernatant. Six fractions were obtained by eluting with 20%, 30%, 45%, 60%, 90% and 100% of acetonitrile. These fractions were dried using a speed-vac, then, taken with DMEM. Tests on Caco-2 cells stimulated by IL-1, showed an anti-inflammatory effect for a fraction of supernatant eluted with 90% acetonitrile.

1.3. Comparative Mass Spectrometry Analysis of *F. prausnitzii* Culture Medium.

The "active" fractions eluted with 90% of acetonitrile were then analysed to detect molecules specific of the culture supernatant of *F. prausnitzii*. The MALDI-TOF mass spectra of LyBHI and culture supernatant were obtained from Voyager® DE Pro (AB-Sciex) in the linear and reflector positive mode, using a nitrogen UV laser (337 nm, laser 3 Hz, pulse 3 ns) and a matrix of 100 mM α-cyano-4-hydroxycinnamic acid (CHCA) in 70/30% (v/v) acetonitrile/water TFA 0.1% solution. Spectra were obtained with an extraction delay of 125 ns (for the reflector mode) or 300 ns (for the linear mode), an accelerating voltage of 20 kV and an averaging of 300 laser shots per sample. The mass range studied is from 500 to 4000 Da for the reflector mode and from 3500 to 30 000 Da for the linear mode.

Six ions (m/z 1733.93; 1832.92; 1946.97; 2047.95, 2146.94 et 4601.06) were identified in the *F. prausnitzii* supernatant fraction eluted with 90% of acetonitrile. No difference between the culture medium LyBHI and the *F. prausnitzii* supernatant was observed in the other fractions of medium.

1.4. Identification of Molecules by a FT-ICR Mass Spectrometer.

The ions of interest were fragmented by a FT-ICR mass spectrometer, equipped with a 7T superconducting magnet (ApexQe®, Bruker Daltonics, Bremen, Germany). Mass spectral data were acquired in the broadband mode over an m/z range of 150 to 1500 with 256 k data points, leading to the registration of a transient signal of 0.17 s. Data processing and data acquisition were performed using respectively Apex Control® version 2.1 software and Data Analysis® version 3.4 (Bruker Daltonics). Mass values displayed correspond to the monoisotopic masses. The mass spectra obtained for these six ions correspond to spectra of fragmentation peptides. Thus, a de novo sequencing of the six peptides was necessary to obtain a sequence of amino acids.

1.5. De Novo Sequencing of the Six Peptides.

The freeze-dried fractions were resuspended in a mixture methanol/water containing, 0.5% formic acid and directly infused into the hybrid mass spectrometer Qh-FT/ICR. Mass spectra were recorded in positive mode ionization. The kinetic energy was 4 eV for the registration of a mass spectrum and about 15 eV for a spectrum of product ions. The accumulation time of ions in the collision cell, acting as a linear trap, were 0.5 s. The transfer time of ions between the collision cell and the ICR cell was set at 0.001 sec. The ions were trapped in the ICR cell by a trapping potential of 2V, and this potential is reduced to 1 V for the step excitation/detection.

Here are the sequences of amino acids obtained by de novo sequencing:

```
Peptide 1
GNTF[I/L]QST[I/L]NRT[I/L]GV[I/L]

Peptide 2
VGNTF[I/L]QST[I/L]NRT[I/L]GV[I/L]

Peptide 3
[I/L]VGNTF[I/L]QST[I/L]NRT[I/L]G-V[I/L]

Peptide 4
T[I/L]VGNTF[I/L]QST[I/L]NRT[I/L]GV[I/L]

Peptide 5
VT[I/L]VGNTF[I/L]QST[I/L]NRT[I/L]GV[I/L]

Peptide 6
FSGNTTWKEVGNIGKNLFGTNVKGNPIEKNNFGDYAMNALGIA
```

Peptide 1 corresponds to the peptide defined by the sequence SEQ ID NO: 35 described above, peptide 2 corresponds to the peptide defined by the sequence SEQ ID NO: 36 described above, peptide 3 corresponds to the peptide defined by the sequence SEQ ID NO: 37 described above, peptide 4 corresponds to the peptide defined by the sequence SEQ ID NO: 38 described above, peptide 5 corresponds to the peptide defined by the sequence SEQ ID NO: 39 described above, peptide 6 corresponds to the peptide defined by the sequence SEQ ID NO: 34 described above.

The identification of residues leucine and isoleucine were initially undefined because they are isomeric amino acids and the genome of *F. prausnitzii* was not sequenced.

1.5. In Silico Analysis of the Six Peptides

As soon as the genome of *F. prausnitzii* was sequenced, the in silico analysis (NCBInr) allowed to confirm that these six peptides are all derived from one *F. prausnitzii* A2-165 protein ZP 05614546.1 (Accession number changed to WP_005932151; SEQ ID NO: 2) conserved hypothetical protein (E-value: $10^{-9}$) and to remove the ambiguity between leucine and isoleucine.

This analysis also allowed to detect a posteriori three other peptides from this protein ZP 05614546.1 (Accession number changed to WP_005932151; SEQ ID NO: 2) in this active fraction, with a very low intensity on the MS-spectra.

```
Peptide 7
NTFLQSTINRTIGVL

Peptide 8
AAVYNLGVAPTKNTVKETEVKFTV

Peptide 9
NYSVIAENEMTYVNGGANFIDAIGAVTAPIWTLDNVKTFNTNIVT LV
```

Peptide 7 corresponds to the peptide defined by the sequence SEQ ID NO: 44 described above, peptide 8 corresponds to the peptide defined by the sequence SEQ ID NO: 45 described above, peptide 9 corresponds to the peptide defined by the sequence SEQ ID NO: 46 described above.

In this first part, the inventors identified nine peptides which were detected only in the supernatant of *F. prausnitzii*. These peptides were present in eluted active fraction from the supernatant of *F. prausnitzii*, and absent from control fractions, without inflammatory effect.

The inventors thus identified anti-inflammatory peptides, all issued from a protein (ZP 05614546.1, Accession number changed to WP_005932151; SEQ ID NO: 2) of 14 491,350 Da synthesized by *F. prausnitzii*. The function of this protein is unknown.

2. Evaluation of the Anti-Inflammatory Effects of the Protein ZP05614546.1 (Accession Number Changed to WP_005932151; SEQ ID NO: 2) and its Derived Peptides.

In order to confirm that anti-inflammatory effects of *F. prausnitzii* supernatant relies at least in part on ZP05614546.1 (SEQ ID NO: 2) and/or its derived peptides, the inventors tested synthetic protein derived peptides and the ZP05614546.1 protein (SEQ ID NO: 2) itself using two approaches.

2.1. Characterization of the Protein

The inventors studied the different properties of the protein.

First, they identified by alignment on biological databases five orthologs sequences having a significant identity with the sequence of ZP05614546.1. Said sequences seem to belong to other strains of *F. prausnitzii*. These sequences may certainly correspond to orthologs of the protein ZP05614546.1 (FIG. 3). A consensus sequence was obtained from this alignment corresponding to SEQ ID NO: 1.

Interestingly, they noted that the N-terminal part of the protein (about the 80 first amino acids; SEQ ID NO: 32) is highly conserved. A central part of the protein also shows a significant conservation for about 20 amino acids around the 150$^{th}$ amino acids.

Studying the hypothetical structure of the protein, they show that it contains two hydrophobic domains around the position AA20-50 and AA90-120. This second hydrophobic domains corresponds the 20aa domain significantly conserved around the 150$^{th}$ amino acids. Another structural analysis of the sequence shows two hypothetical α-helical regions matching with these two hydrophobic domains.

Based on these analyses, the core structure of the polypeptide of the invention corresponds to an amino acid sequence having, in the N-term to C-term orientation:
  the consensus sequence SEQ ID NO: 32; and
  the consensus sequence SEQ ID NO: 33,
wherein the sequence SEQ ID NO: 32 and SEQ ID NO: 33 are preferably spaced from 80 to 10 amino acids, preferably from 60 to 15 amino acids, and more preferably from 40 to 20 amino acids.

Interestingly, the study of the sequence and structure of the protein seems to show that it does not contain any signal peptide. Some of the fragments identified by the inventors (as described above) correspond to fragments of the conserved regions within the five "orthologs" sequences.

2.2. Direct Incubation of Intestinal Epithelial Cell Models with Protein ZP05614546.1 and the Derived Peptides of Interest The inventors thus incubated intestinal epithelial HT29 cells with the protein and/or with the derived peptides described above.

Using said cells, they did not obtain any result that could show any anti-inflammatory effect using this strategy.

The inventors then incubated mucus secreting intestinal epithelial HT29-MTX cells with two peptide fragments obtained from the protein ZP05614546.1.

```
                                                SEQ ID NO: 47
K G N T F L Q S T I N R T I G V L

SEQ ID NO: 48
V K G N P I E K N N F G D Y A M N A L G I A A A V
Y N L G V A P T K N T V K E T E V K F T V
```

These both peptides defined by the amino acid sequences SEQ ID NO: 47 and SEQ ID NO: 48 respectively correspond to the regions between positions 53 and 68 and 90 and 135 of the protein ZP05614546.1 (SEQ ID NO: 2).

The inventors measured the IL-8 production (as a marker of inflammation) after stimulation of HT29-MTX cells incubated or not with said peptides and stimulated by TNFα. The results show that these both peptides have an anti-inflammatory effect in a dose dependent manner (FIG. 4).

This biological activity observed with the peptides in the HT29-MTX cell model may result from an interaction between the polypeptides of the invention and the mucus.

2.3. Transfection of Protein ZP05614546.1 and Orthologs into Epithelial Cell Models In order to further analyze the activity of the polypeptides of the invention, the inventors decided to transfect the protein-coding cDNA directly into mammalian epithelial cell model.

The sequence of the protein ZP05614546.1 (SEQ ID NO: 2) has been cloned in 3× Flag (C-term) pCMV vector.

Using an NFκB reporter system in human epithelial cells HEK 293T, they showed that the protein ZP05614546.1 inhibits the NFκB signaling pathway in a dose-dependent manner.

Figure 1:
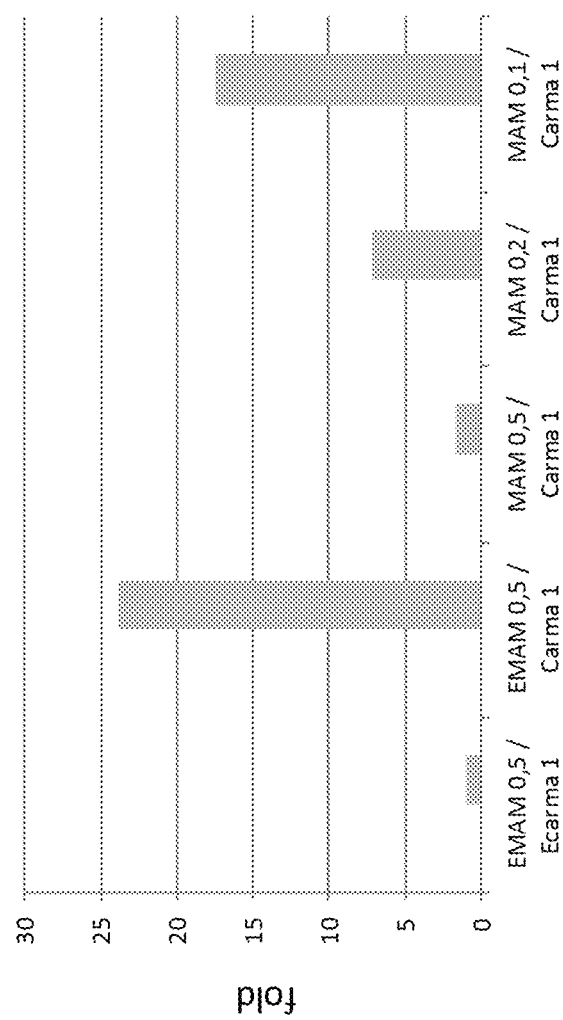
FIG. 1 shows effect of protein ZP05614546.1 (SEQ ID NO: 2) on Carma-1-dependant NF-kB activation using HEK293T cells and NFκB luciferase reporter.

Indeed, the protein ZP05614546.1 inhibits Carma-1-dependent NFκB activation (FIG. 1).

In order to test the NFκB signaling pathway inhibiting activity from the orthologs of ZP05614546.1, the other protein sequences from FIG. 3 were also cloned in 3× Flag (C-term) pCMV vector and tested in the NFκB reporter system in human epithelial cells HEK 293T.

The inhibition of NFκB signaling pathway by some of these proteins is summarized in the following table I:

|  | A2-165 (ZP05614546.1) (SEQ ID NO: 2) | SL3/3 (SEQ ID NO: 3) | M21/2 (SEQ ID NO: 4) | CNCM4573 (SEQ ID NO: . . . ) | L2-62 (SEQ ID NO: . . . ) | KLE1255 (SEQ ID NO: 5) |
|---|---|---|---|---|---|---|
| NFκB signaling pathway inhibition (%) | 58 ± 6 | 86 ± 5 | 90 ± 3 | 89 ± 2 | 34 ± 5 | 72 ± 1 |

The results established that all the tested orthologs of ZP05614546.1 have inhibition properties of NFκB signaling pathway like the ZP05614546.1 protein.

In HEK293T cells stably expressing TLR4, MD2 and CD14, the inventors further showed that the protein ZP05614546.1 inhibits the LPS-dependent NFκB activation (FIG. 2).

Expression of ZP05614546.1 as well as of its orthologs was confirmed in HEK293T cells by Western blot with anti-Flag antibody. In another cell model (HeLa), the expression was validated by immunofluorescence and ZP05614546.1 was localized around the cell nucleus.

So as to better quantify the anti-inflammatory properties of ZP05614546.1 and orthologs, increasing quantity of pCMV plasmid (i.e. 50, 25 and 12.5 ng) containing SEQ ID NO: 2 and SEQ ID NO: 4 were used to transfected HEK293 cell line. Then, the evolution of NFκB signaling pathway expression was determined as previously. The FIG. 9 shows the inhibition percentage of Carma-1-dependant NF-kB activation using HEK293T cells and NFκB luciferase reporter by the protein ZP05614546.1 (SEQ ID NO: 2) and by one of its orthologs (SEQ ID NO: 4). Accordingly, the SEQ ID NO: 4 from the strain M21/2 is 100% (2 fold) more efficient in inhibiting NFκB signaling pathway than the protein ZP05614546.1.

2.4. Determination of the Domains of Protein ZP05614546.1 and Orthologs Involved in Anti-Inflammatory Properties In order to further analyze the activity of the polypeptides of the invention, the inventors decided to clone into the previously described pCMV plasmid, the sequences corresponding to amino acids 23-135 of SEQ ID NO: 2 (Mut 1), 1-39/72-135 of SEQ ID NO: 2 (Mut 2), 1-99 of SEQ ID NO: 2 (Mut 3), 35-77 of SEQ ID NO: 2 (p35-'7'7)

and . . . - . . . of SEQ ID NO: 2 from MAM from *F. prausnitzii* strain A2-165. The four constructs, Mut 1, Mut 3, p35-77 and p49-70 carry the peptide 1-5.

The inventors established that the same inhibition rate with the full length ZP05614546.1 (SEQ ID NO: 2) or its mutant Mut 1, Mut 3 and p35-77. When amino-acids 35-77 are missing like in Mut 2 there is no Nf-kB inhibitory activity, indicating that the anti-inflammatory activity of MAM from *F. prausnitzii* strain A2-165 is carried by its peptide 35-77 (FIG. 10). In one experiment, 49-70 has also shown a strong inhibitory activity supporting the fact that most of this inhibitory activity is carried out by this portion (data not shown).

In conclusion, the inventors showed that, even if the first results seem to show the contrary, the protein ZP05614546.1, its orthologs and its derived peptides described above have an anti-inflammatory effect.

Example 2. Use of Anti-Inflammatory Effects of the Protein of the Invention

Constructions

Secreted form of the protein ZP05614546.1 (SEQ ID NO: 2) was expressed in a NICE (Nisine Induced Controlled Expression) host system (*L. lactis* strain NZ9000), using a expression cassette pSEC wherein the gene encoding ZP05614546.1 (SEQ ID NO: 2) is cloned downstream to the pNis promoter and a Usp45signal peptide. The plasmid harbors a resistance gene to chloramphenicol.

The gene encoding ZP05614546.1 (SEQ ID NO: 2) is produced by synthesis in order to optimize the codons for *L. lactis* for a better expression of the protein in this host cell. The gene is digested by restriction enzymes compatible with those digesting the pSEC vecteur (NsiI, SpeI). The ligation between the vector and the insert generates a plasmid which is introduced into the NZ9000 strain by electroporation.

The clones that grow on a medium comprising M17 medium+glucose 0.5%+Chloramphenicol 10 µg/mL are analyzed for the presence of the inserts coding for the protein ZP05614546.1 (SEQ ID NO: 2) The purified plasmid comprising the insert is sequenced in order to confirm the integrity of the nucleic acid sequence encoding the protein of interest in said plasmid. After its sequence confirmed, the plasmid is transferred in strains NZ9000 (Htra-), NZ9000 (Clp-) and NZ9000 (Htra-/Clp-).

The strains that contain the plasmid encoding the protein ZP05614546.1 (SEQ ID NO: 2) is re-introduced on a medium comprising M17+glucose 0.5%+Chloramphenicol 10 µg/mL and incubated during the night at 30° C. The morning after that, the strain is diluted at 1/100. Expression of the protein is induced with nisine at 10 ng/mL during one hour at 30° C. A protein extraction is further realized by separating the centrifugate and the supernatant and by treating them differently. The proteins present in the supernatant are precipitated with TCA and centrifuged during 30 min, and then they are introduced in a Laemmli buffer. The centrifugate is mixed in PBS comprising antiprotease and is sonicated at a 6*10 sec cycle. The lysate is centrifuged in order to eliminate the bacterium fragments and the supernatant which contains a lot of proteins is kept for further studies.

The constructions may be realized in another plasmid (an optimized plasmid similar to the previous one) that permits a better secretion of the proteins of interest: the presence of a nucleic aid sequence encoding a polypeptide of 9 amino acids (LEISSTCD, SEQ ID NO: 22) placed between the nucleic acid sequence encoding the signal peptide and the nucleic acid sequence encoding one of the protein of interest adds two negative charges to the protein, allowing a better transport through the bacterium membrane.

Cloning is done by introduction of the nucleic acid sequence encoding the proteins of interest in such plasmids as described above. Said plasmids are introduced in the NZ9000 WT strain and in the NZ9000 Htra-strain (deficient in its extern protease).

Another construction is envisaged, that permits a cytoplasmic form of the proteins of interest. It consists in the fusion of the nucleic acid sequence encoding the proteins of interest with the promoter pNis without the Usp45 signal peptide. The cytoplasmic form of said proteins allows the protection of the protein in hard extern conditions.

Cloning and expression of the proteins are made as describe above. The supernatant of bacteria expressing the proteins is not analyzed as the protein is not anymore secreted.

In Vitro Studies of the Anti-Inflammatory Effects of the Protein and its Derived Fragments.

HT29 epithelial cells are in a DMEM medium comprising 10% serum SVF and 1% glutamine at a concentration of 0.1 $10^6$ cells/mL. The cells are plated in 24-wells plates (500 µL of medium by well). The plates are placed at 37° C. in a 10% $CO_2$ sterilizing room during 72 h.

Culture medium is changed 3 times and cells incubated during 24 h each time. Then, cells are stressed in a DMEM medium comprising 5% serum SVF and 1% glutamine is added (500 µL by well). The plates are placed at 37° C. in a 10% $CO_2$ sterilizing room during 24 h.

After that, HT29 cells are co-incubated with bacteria expressing the protein ZP05614546.1 (SEQ ID NO: 2; at a ratio 1/40) or its ortholog (SEQ ID NO: 4; at a ratio 1/40) and supernatants are recovered.

Media comprises DMEM, 5% SFV serum, 1% glutamine, with or without TNFα at a concentration of 5 ng/µL, with or without antibiotics PS 0.1%.

Bacteria cultures are centrifuged a 3000 g during 5 min, centrifugates are recovered in 1 mL DMEM and centrifuged again at 3000 g during 5 min. Centrifugates are recovered in 1 mL DMEM+5% SVF serum+1% glutamine.

DMEM is eliminated, 450 µL/well of medium comprising DMEM+5% SVF serum+1% glutamine+0.1% PS or DMEM+5% SVF serum+1% glutamine+0.1% PS+TNFα is added. 50 µL of bacterium solution. The control does not comprise bacteria solution.

Plates are placed in CO2 sterilizing room at 37° C. during 6 h.

Supernatant of cultures are recovered and stocked.

In Vivo Studies of the Anti-Inflammatory Effects of the Protein and its Derived Fragments.

C57B16 mice (6-8 weeks old) are kept at room temperature, under 12 h light/dark cycles and having free access to food and water, except the day before the induction of colitis, where they are fasted for 12 h.

Colonic inflammation is induced by treatments with Dextran Sodium Sulfate (DBNS). In details, DSS is dissolved in drinking water (3 or 5% wt/vol) and the animals are free to drink this solution for 7-days. Water consumption is measured in the DSS-treated groups and compared to groups of naïve mice drinking water: no difference is observed for the volume of liquid consumed, between water and DSS-drinking mice. Mice are treated daily orally, with 200 µL of 1 to $5.10^9$ colony forming units (cfu) of strains to be tested or bacterial milieu alone—i.e. *L. lactis* expressing the protein ZP 05614546.1 (Accession number changed to WP_005932151), its ortholog of strain M21/2 (SEQ ID NO:

4) or no protein-. The first treatment starts at the same time DSS is added to drinking water (but it can also be performed in advance, as a preventive treatment) and the last treatment is on the day of the sacrifice (day 7). Body weight and survival rate are measured daily after the induction of colitis (or right after the first gavage, in case of preventive treatment). DAI (disease activity index is also measured):

The Disease activity index (Cooper HS Lab Invest 1993; 69:238-49) is carried out each day (as showed in the table below).

|  | Description | Score |
| --- | --- | --- |
| Diarrhea | Normal | 0 |
|  | Soft | 2 |
|  | Liquid | 4 |
| Blood in faeces | No | 0 |
|  | Low | 2 |
|  | important | 4 |
| Loose of weight | <1% | 0 |
|  | 1-5% | 1 |
|  | 5-10% | 2 |
|  | 10-15% | 3 |
|  | >15% | 4 |
| Activity Score |  | Sum of the 3 scores |

The FIG. 5 shows the body weight evolution in the DNBS inflammation model for control mice ( ) and ZP 05614546.1 daily treated mice (Δ).

The FIG. 6 shows the activity score observed at day 3 following colonic inflammation induction by DNBS for control mice ( ) and ZP 05614546.1 daily treated mice (Δ).

On day 7 after adding DSS to their drinking water, mice are sacrificed and colons are harvested for measure of several parameters of inflammation: bowel thickness and length, myeloperoxydase (MPO) activity, cytokine expression (IL-17A, IFN-γ, IL10, IL12p70 or other cytokines) can be measured. Colon washes are also performed with 1 ml of PBS+ anti-protease cocktail. 400-500 µl of blood are collected for cytokine analysis.

The FIG. 7 and FIG. 8 show the IL-17A and IFN-γ expression respectively for control mice ( ) and ZP 05614546.1 daily treated mice (Δ).

Finally, the in vivo results confirm the previous in vitro results establishing that the ZP 05614546.1 protein significantly reduce colonic inflammation. The results have further established that the reduction of colonic inflammation by ZP 05614546.1 ortholog of strain M21/2 (SEQ ID NO: 4) was upper than the one observed with ZP 05614546.1 protein (data not shown).

The invention claimed is:

1. A method for treating an inflammatory bowel disease in a patient in need thereof, said method comprising administrating to said patient a therapeutically effective amount of a host cell genetically engineered to express a nucleic acid sequence encoding a polypeptide consisting of the amino acid sequence set forth by SEQ ID NO: 10.

2. The method of claim 1, wherein the inflammatory bowel disease is selected from the group consisting of Crohn disease, ulcerative colitis, ileitis and enteritis.

3. The method of claim 1, wherein said inflammatory disease is Crohn disease.

4. A method for treating an inflammatory bowel disease in a patient in need thereof, said method comprising administrating to said patient a therapeutically effective amount of an isolated polypeptide consisting of the amino acid sequence set forth by SEQ ID NO: 10 formulated with a pharmaceutically acceptable carrier.

5. The method of claim 1, wherein said inflammatory bowel disease is an inflammatory bowel disease resulting from the activation of the NFκB pathway.

6. The method of claim 4, wherein said isolated polypeptide is isolated from the *Faecalibacterium prausnitzii* strain CNCM 1-4573 or from the supernatant of the *Faecalibacterium prausnitzii* strain CNCM 1-4573.

7. The method of claim 4, wherein the inflammatory bowel disease is selected from the group consisting of Crohn disease, ulcerative colitis, ileitis and enteritis.

8. The method of claim 4, wherein said inflammatory disease is Crohn disease.

9. The method of claim 4, wherein said inflammatory bowel disease is an inflammatory bowel disease resulting from the activation of the NFκB pathway.

\* \* \* \* \*